(12) United States Patent
Zu et al.

(10) Patent No.: US 10,214,776 B2
(45) Date of Patent: Feb. 26, 2019

(54) NANOPROBE-BASED GENETIC TESTING

(71) Applicant: Agency for Science, Technology and Research, Singapore (SG)

(72) Inventors: Yanbing Zu, Singapore (SG); Jackie Y. Ying, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 461 days.

(21) Appl. No.: 14/783,392

(22) PCT Filed: Apr. 4, 2014

(86) PCT No.: PCT/SG2014/000150
§ 371 (c)(1),
(2) Date: Oct. 8, 2015

(87) PCT Pub. No.: WO2014/168582
PCT Pub. Date: Oct. 16, 2014

(65) Prior Publication Data
US 2016/0046993 A1 Feb. 18, 2016

(30) Foreign Application Priority Data
Apr. 11, 2013 (SG) ................. 201302745-3

(51) Int. Cl.
*C12Q 1/6827* (2018.01)
*C12Q 1/6883* (2018.01)
*B82Y 15/00* (2011.01)

(52) U.S. Cl.
CPC ............ *C12Q 1/6883* (2013.01); *B82Y 15/00* (2013.01); *C12Q 1/6827* (2013.01); *C12Q 2600/156* (2013.01)

(58) Field of Classification Search
None
See application file for complete search history.

(56) References Cited

U.S. PATENT DOCUMENTS

2008/0085839 A1  4/2008  Klapproth
2009/0197246 A1*  8/2009  Stropp ................. C12N 9/1007
                                              435/6.12

FOREIGN PATENT DOCUMENTS

CN    102884204 A    1/2013
WO    2011087456 A1  7/2011

OTHER PUBLICATIONS

Extended European Search Report for European Patent Application No. 14 783 008.7 dated Oct. 25, 2016, pp. 1-9.
Cao et al., "A Two-Color-Change, Nanoparticle-Based Method for DNA Detection," Talanta, vol. 67, No. 3, 2005, pp. 449-455.
Zu et al., "Nanoprobe-based Genetic Testing," Nano Today, vol. 9, 2014, pp. 166-171.
Martins et al., "Amorphous/Nanocrystalline Silicon Biosensor for the Specific Identification of Unamplified Nucleic Acid Sequences Using Gold Nanoparticle Probes," Applied Physics Letters, vol. 90, 2007, pp. 1-3.
Doria et al., "Nanodiagnostics: Fast Colorimetric Method for Single Nucleotide Polymorphism/Mutation Detection," IET Nanobiotechnol., vol. 1, No. 4, 2007, pp. 53-57.
Larguinho et al., "Gold and Silver Nanoparticles for Clinical Diagnostics—From Genomics to Proteomics," Journal of Proteomics, vol. 75, 2012, pp. 2811-2823.
International Preliminary Report on Patentability for International Application No. PCT/SG2014/000150 dated Oct. 13, 2015, pp. 1-6.
Office Action for Chinese Patent Application No. 201480029699.2 issued from State Intellectual Property Office of P.R. China dated Jul. 18, 2017, pp. 1-16.
Written Opinion for International Application No. PCT/SG2014/000150 dated Jun. 13, 2014, pp. 1-12.
Ann K. Daly, "Genome-Wide Association Studies in Pharmacogenomics," Nat. Rev. Genet. vol. 11, Apr. 2010, pp. 241-246.
Evans et al., "Pharmacogenomics: Translating Functional Genomics into Rational Therapeutics," Science, vol. 286, Oct. 15, 1999, pp. 487-491.
Gage et al., "Use of Pharmacogenetics and Clinical Factors to Predict the Maintenance Dose of Warfarin," www.thrombosis-online.com, vol. 91, 2004, pp. 87-94.
Rieder et al., "Effect of VKORC1 Haplotypes on Transcriptional Regulation and Warfarin Dose," N. Engl. J. Med. vol. 352, Jun. 2, 2005, pp. 2285-2293.
Wen et al., "Prospective Study of Warfarin Dosage Requirements Based on CYP2C9 and VKORC1 Genotypes," Clin. Pharma. Ther., vol. 84, Jul. 2008, pp. 83-89.
The International Warfarin Pharmacogenetics Consortium, "Estimation of the Warfarin Dose with Clinical and Pharmacogenetic Data," N. Engl. J. Med., vol. 360, Feb. 19, 2009, pp. 753-764.
"Highlights of Prescribing Information" for Coumadin, 2010, http://packageinserts.bms.com/pi/pi_coumadin.pdf, Accessed Dec. 4, 2012, pp. 1-12.
Epstein et al., "Warfarin Genotyping Reduces Hospitalization Rates," J. Am. Coll. Cardiol, vol. 55, No. 25, 2010, pp. 2804-2812.

(Continued)

*Primary Examiner* — Robert T. Crow
(74) *Attorney, Agent, or Firm* — Winstead, P.C.

(57) ABSTRACT

The present application relates to methods of detecting a mutation in a target nucleic acid molecule. Two phosphorodiamidate morpholino oligomer probes that differ by at least one base are each covalently coupled to a nano article and hybridized to a target sequence. The melting temperature of the complexes between each of the two probes and the target nucleic acid are measured and compared to determine whether the sample contains a nucleic acid with the mutation. Further, the present invention relates to kits comprising a first and second conjugate as described herein and to the use of such kits for the detection of mutations in a target nucleic acid molecule or for assigning a genotype to a target nucleic acid molecule.

20 Claims, 21 Drawing Sheets
Specification includes a Sequence Listing.

(56) References Cited

OTHER PUBLICATIONS

Anderson et al., "A Randomized and Clinical Effectiveness Trial Comparing Two Pharmacogenetic Algorithms and Standard Care for Individualizing Warfarin Dosing (CoumaGen-II)," Circulation, vol. 125, Apr. 24, 2012, pp. 1997-2005.

Kim et al., "SNP Genotyping: Technologies and Biomedical Applications," A. Annu. Rev. Biomed. Eng., vol. 9, 2007, pp. 289-320.

Chen et al., "Single Nucleotide Polymorphism Genotyping: Biochemistry, Protocol, Cost and Throughput," Pharmacogenomics J., vol. 3, Feb. 10, 2003, pp. 77-96.

You et al., "Cost-Effectiveness of Dabigatran Versus Genotype-Guided Management of Warfarin Therapy for Stroke Prevention in Patients with Atrial Fibrillation," Expert Opin. Pharmacol., vol. 7, Issue 6, Jun. 2012, pp. 1-9.

Milbury et al., "PCR-Based Methods for the Enrichment of Minority Alleles and Mutations," Clin. Chem., vol. 55, No. 4, 2009, pp. 632-640.

Zu et al., "Visualizing Low-Level Point Mutations: Enzyme-Like Selectivity Offered by Nanoparticle Probes," Small, vol. 7, No. 3, 2011, pp. 306-310.

Hollstein et al., "p53 Mutations in Human Cancers," Science, vol. 253, 1992, pp. 49-53.

Bartek et al., "Genetic and Immunochemical Analysis of Mutant p53 in Human Breast Cancer Cell Lines," Oncogene, vol. 5, 1990, pp. 893-899.

Higuchi et al., "Production of Single-Stranded DNA Templates by Exonuclease Digestion Following the Polymerase Chain Reaction," Nucleic Acids Res., vol. 17, No. 14, 1989, pp. 5865-5865.

Ross, et al., "Worldwide Allele Frequency Distribution of Four Polymorphisms Associated with Warfarin Dose Requirements," Journal of Human Genetics, vol. 55, 2010, pp. 582-589.

Jin et al., "What Controls the Melting Properties of DNA-Linked Gold Nanoparticle Assemblies?" Journal of the American Chemical Society, vol. 125, 2003, pp. 1643-1654.

* cited by examiner

1. Ladder, 2. NTC, 3. MCF-7, 4. MDA-MB-231

| Initial Denaturing | 95°C | 3 min |
|---|---|---|
| 10-Cycle Touchdown | 95°C | 20 sec |
| | 62°C, -1°C/cycle | 20 sec |
| | 72°C | 25 sec |
| 40-Cycle Amplification | 95°C | 15 sec |
| | 57°C | 20 sec |
| | 72°C | 25 sec |
| End | 4°C | Hold |

Figure 17

|  | CYP2C9*2 SNP | CYP2C9*3 SNP | VKORC1-1639 SNP |
|---|---|---|---|
| $T_{m,}^{WT}$ | 55°C | 42°C | 42°C |
| $T_{m,}^{MUT}$ | 47°C | 35°C | 50°C |
| Genotype | *1/*1 | *1/*1 | AA |

SEQUENCE LISTING

<160> NUMBER OF SEQ ID NOS: 24

<210> SEQ ID NO 1
<211> LENGTH: 25
<212> TYPE: DNA
<213> ORGANISM: Artificial Sequence

```
<220> FEATURE:
<223> OTHER INFORMATION: synthetic nucleic acid molecule

<400> SEQUENCE: 1
cggtctctcc caggattttt ttttt                                          25

<210> SEQ ID NO 2
<211> LENGTH: 25
<212> TYPE: DNA
<213> ORGANISM: Artificial Sequence
<220> FEATURE:
<223> OTHER INFORMATION: synthetic nucleic acid molecule

<400> SEQUENCE: 2
cggtctttcc caggattttt ttttt                                          25

<210> SEQ ID NO 3
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of p53

<400> SEQUENCE: 3
ctactgggac ggaacagctt tgaggtgcgt gtttgtgcct gtcctgggag agaccggcgc    60
acagaggaag agaatctccg caagaaaggg gagcctcacc a                       101

<210> SEQ ID NO 4
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of p53

<400> SEQUENCE: 4
ctactgggac ggaacagctt tgaggtgcgt gtttgtgcct gtcctgggaa agaccggcgc    60
acagaggaag agaatctccg caagaaaggg gagcctcacc a                       101

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
gacaagggtg gttgggagta g                                              21

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
gcaaggaaag gtgataaaag tgaa                                           24

<210> SEQ ID NO 7
<211> LENGTH: 25
<212> TYPE: DNA
<213> ORGANISM: Artificial Sequence
<220> FEATURE:
```

<223> OTHER INFORMATION: synthetic nucleic acid molecule

<400> SEQUENCE: 7
cacggtcctc aatgcttttt ttttt                                    25

<210> SEQ ID NO 8
<211> LENGTH: 25
<212> TYPE: DNA
<213> ORGANISM: Artificial Sequence
<220> FEATURE:
<223> OTHER INFORMATION: synthetic nucleic acid molecule

<400> SEQUENCE: 8
cacagtcctc aatgcttttt ttttt                                    25

<210> SEQ ID NO 9
<211> LENGTH: 25
<212> TYPE: DNA
<213> ORGANISM: Artificial Sequence
<220> FEATURE:
<223> OTHER INFORMATION: synthetic nucleic acid molecule

<400> SEQUENCE: 9
aggtcaatgt atctcttttt ttttt                                    25

<210> SEQ ID NO 10
<211> LENGTH: 25
<212> TYPE: DNA
<213> ORGANISM: Artificial Sequence
<220> FEATURE:
<223> OTHER INFORMATION: synthetic nucleic acid molecule

<400> SEQUENCE: 10
aggtcaaggt atctcttttt ttttt                                    25

<210> SEQ ID NO 11
<211> LENGTH: 25
<212> TYPE: DNA
<213> ORGANISM: Artificial Sequence
<220> FEATURE:
<223> OTHER INFORMATION: synthetic nucleic acid molecule

<400> SEQUENCE: 11
accgcacccg gccaattttt ttttt                                    25

<210> SEQ ID NO 12
<211> LENGTH: 25
<212> TYPE: DNA
<213> ORGANISM: Artificial Sequence
<220> FEATURE:
<223> OTHER INFORMATION: synthtetic nucleic acid molecule

<400> SEQUENCE: 12
accgcacctg gccaattttt ttttt                                    25

<210> SEQ ID NO 13
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of CYP2C9

<400> SEQUENCE: 13
ccctcatgac gctgcggaat tttgggatgg ggaagaggag cattgaggac cgtgttcaag    60
aggaagcccg ctgccttgtg gaggagttga gaaaaaccaa g             101

<210> SEQ ID NO 14
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of CYP2C9

<400> SEQUENCE: 14
ccctcatgac gctgcggaat tttgggatgg ggaagaggag cattgaggac tgtgttcaag     60
aggaagcccg ctgccttgtg gaggagttga gaaaaaccaa g             101

<210> SEQ ID NO 15
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of CYP2C9

<400> SEQUENCE: 15
ggagccacat gccctacaca gatgctgtgg tgcacgaggt ccagagatac attgaccttc     60
tccccaccag cctgccccat gcagtgacct gtgacattaa a             101

<210> SEQ ID NO 16
<211> LENGTH: 101
<212> TYPE: DNA
<213> ORGANISM: Artificial Sequence
<220> FEATURE:
<223> OTHER INFORMATION: oligonucleotide containing a nucleic acid
      sequence of CYP2C9

<400> SEQUENCE: 16
ggagccacat gccctacaca gatgctgtgg tgcacgaggt ccagagatac cttgaccttc     60
tccccaccag cctgccccat gcagtgacct gtgacattaa a             101

<210> SEQ ID NO 17
<211> LENGTH: 93
<212> TYPE: DNA
<213> ORGANISM: Artificial Sequence
<220> FEATURE:
<223> OTHER INFORMATION: oligonucleotide containing a nucleic acid
      sequence of VKORC1

<400> SEQUENCE: 17
atccctctgg gaagtcaagc aagagaagac ctgaaaaaca accattggcc gggtgcggtg     60
gctcacgcct ataatcctag cattttggga ggc              93

<210> SEQ ID NO 18
<211> LENGTH: 93
<212> TYPE: DNA
<213> ORGANISM: Artificial Sequence
<220> FEATURE:
<223> OTHER INFORMATION: oligonucleotide containing a nucleic acid
      sequence of VKORC1

<400> SEQUENCE: 18
atccctctgg gaagtcaagc aagagaagac ctgaaaaaca accattggcc aggtgcggtg     60
gctcacgcct ataatcctag cattttggga ggc              93

<210> SEQ ID NO 19

```
<211> LENGTH: 24
<212> TYPE: DNA
<213> ORGANISM: Artificial Sequence
<220> FEATURE:
<223> OTHER INFORMATION: PCR primer

<400> SEQUENCE: 19
cctgggatct ccctcctagt ttcg                                          24

<210> SEQ ID NO 20
<211> LENGTH: 23
<212> TYPE: DNA
<213> ORGANISM: Artificial Sequence
<220> FEATURE:
<223> OTHER INFORMATION: PCR primer

<400> SEQUENCE: 20
ggagtagggt cacccaccct tgg                                           23

<210> SEQ ID NO 21
<211> LENGTH: 21
<212> TYPE: DNA
<213> ORGANISM: Artificial Sequence
<220> FEATURE:
<223> OTHER INFORMATION: PCR primer

<400> SEQUENCE: 21
gcatgcaaga caggagccac a                                             21

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
tggagaacac acactgccag aca                                           23

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
gggtaggtgc aacagtaagg                                               20

<210> SEQ ID NO 24
<211> LENGTH: 24
<212> TYPE: DNA
<213> ORGANISM: Artificial Sequence
<220> FEATURE:
<223> OTHER INFORMATION: PCR primer

<400> SEQUENCE: 24
ctcccaaaat gctaggatta tagg                                          24
```

NANOPROBE-BASED GENETIC TESTING

FIELD OF THE INVENTION

The present invention lies in the field of biochemistry and relates to methods of detecting a mutation in a target nucleic acid molecule. Further, the present invention relates to kits comprising a first and second conjugate as described herein and the use of such kits for the detection of mutations in a target nucleic acid molecule or for assigning a genotype to a target nucleic acid.

BACKGROUND OF THE INVENTION

Genome-wide association studies increasingly link human genetic variants to individual's response towards therapeutic agents. This increased knowledge greatly accelerates progress in personalized medicine. By identifying the genetic hotspots that are associated with drug efficacy and safety, pharmacogenomic (PGx) strategy allows for more individualized drug therapies based on the genetic make-up of patients. In turn, the individualized drug therapies may minimize side effects and improve outcomes (Daly, A K (2010) Nat Rev Genet, 11, 241-246). Already today, PGx information has been incorporated into a number of drug labels to assist clinicians to make therapeutic decisions.

One example is the PGx-guided warfarin dosing. Warfarin is the most widely described oral anticoagulant drug. Despite its effectiveness, warfarin is among the top 10 drugs with serious adverse event reports because of the narrow therapeutic index and the highly variable inter-individual dosing requirements. Therefore, it is important to monitor the anticoagulation status frequently with the International Normalized Ratio (INR), especially in the early period after the initiation of warfarin therapy. The lack of information available in identifying the appropriate initial dose usually leads to multiple dose adjustments and excesses risk of thromboembolic events or bleeding. In the last decade, PGx studies revealed correlations of the warfarin dose requirements and the presence of several genetic single-nucleotide polymorphisms (SNPs). The most significantly related SNPs include two coding variations in the cytochrome P450 enzyme CYP2C9 gene, CYP2C9*2 (rs 1799853) and CYP2C9*3 (rs1057910), and one variation in the vitamin K epoxide reductase complex 1 (VKORC1) gene, promoter SNP-1639G>A (rs9923231) (The International Warfarin Pharmacogenetics Consortium (2009) N Engl J Med, 360, 753-764). These SNPs may explain up to 35% of interpatient warfarin dose variability. In 2010, US FDA updated the labeling for warfarin with PGx-guided dosing ranges (Highlights of prescribing information. Coumadin (2010) http://packageinserts.bms.com/pi/pi_coumadin.pdf). The starting dose could be predicted by referring to a table containing stable maintenance doses observed in multiple patients having different combinations of CYP2C9 and VKORC1 variants. A dosing algorithm incorporating traditional clinical factors and patient genetic status is also available. Recently, a large-scale prospective study found that PGx-guided warfarin therapy reduced hospitalization rates for patients that just started a warfarin therapy by ~30% (Epstein, R S et al. (2010) J Am Coll Cardiol, 22, 2804-2812). A randomized clinical trial, CoumaGen-II, provided further evidence for the clinical benefit of incorporating genotype knowledge into dosage selection (Anderson, J L et al. (2012) Circulation, 125, 1997-2005). As the value of warfarin genotyping is being supported by more and more clinical trials, increasing importance of the PGx results for clinical practice can be expected. Rapid and cost-effective genotype testing would greatly facilitate this process.

Currently available genotyping platforms include DNA microarray, real-time polymerase chain reaction (PCR), single-base extension, and high-resolution melting analysis (Kim, S and Misra, A (2007) Annu Rev Biomed Eng, 9, 289-320). Although these platforms are very useful in high-throughput studies, they are less cost-effective in on-demand clinical testing because of the expensive instruments and reagents involved (Joyce, H S (2011) Expert Opin Pharmacol, 12, 435-441). Four commercial assays have been approved by the FDA for warfarin-sensitivity genotyping, including Infinity Warfarin Assay (Autogenomics, Inc., Vista, Calif., USA), eSensor Warfarin Sensitivity Test (GenMark Diagnostics, Inc., Carlsbad, Calif., USA), eQ-PCR LC Warfarin Genotyping Kit (TrimGen, Sparks, Md., USA), and Verigene Warfarin Metabolism Nucleic Acid Test (Nanosphere, NorthBrook, Ill., USA). Some of these assays target point-of-care applications, but special instruments are required to conduct the testing.

Genotype analysis of highly heterogeneous specimens, such as tumor samples, is much more challenging than SNP genotyping because the somatic mutation detection has to be conducted in a large wild-type DNA background. For a heterozygous SNP sample, the MUT/WT allele ratio is 50%, while the ratio may be less than 10% for somatic mutation in a tumor specimen. A highly sensitive detection method is required to gauge the mutations. Usually, enrichment of the mutant sequences by allele-specific PCR or PCR clamping strategies are employed to achieve high sensitivity (Milbury, C A (2009) Clin Chem, 55, 632-640).

Recently, a new type of plasmonic nanoparticle (NP) probes, gold NPs functionalized with nonionic morpholino oligonucleotides (MORs) was prepared (Zu, Y et al. (2011) Small, 7, 306-310). The detection of DNA targets is based on the change of nanoprobe stability upon hybridization, i.e., the nanoprobes become more stable when bound to negatively charged DNA targets. The NP stability variation can be revealed simply by adding salt to the solution. The target-stabilized nanoprobes remain red in color, while the nanoprobes with no DNA attached would aggregate, leading to solution color change. The targets with similar sequences can be differentiated by various melting transition temperatures ($T_m$) of the target-probe hybrids (FIG. 1). The extremely sharp transition ensures the high detection specificity.

However, because of the low sensitivity of the nanoprobe-based method (detection limit ~1 nM), genes cannot be analyzed directly. Prior to detection, amplification of the target sequence by PCR is necessary. In the present study, it has been found that the value of $T_m$ is highly dependent on the target concentration and can be influenced significantly by the presence of salt in the assay solution. As PCR yield is usually unknown and different master solutions may contain various salt components, it is difficult to analyze PCR products by using a single set of nanoprobes and different, amplified template DNA molecules. Such detection method is described in WO 2011/087456.

Thus, despite major research efforts in recent years, no robust genetic testing platform has been develop yet that allows the determination of genotypes in combination with point-of-care use. Nonetheless, to accelerates progress in personalized medicine there is need in the art for such genetic testing platforms.

SUMMARY OF THE INVENTION

It is an object of the present invention to meet the above need by providing a composition comprising or consisting of a first and second conjugate as described herein. Surprisingly, the inventors have found that the use of at least two different conjugates (each of these conjugates comprise a oligonucleotide analog and a nanoparticle) allows the detection of SNP (single-nucleotide polymorphism) mutations without the use of a second, amplified template DNA molecule, so called control or reference molecule. Herein, a robust genetic testing platform based on a dual-nanoprobe assay is presented, whereby a pair of nanoprobes is employed to allow unambiguous determination of the genotype. The platform utilizes asymmetric PCR (aPCR) for target sequence amplification, and colorimetric signals for end-point detection. The only equipment required for detection is a standard thermal cycler. The assay signals can be visualized by the naked eye or recorded by a digital camera. Therefore, the platform significantly reduces capital investment in instruments and reagents, and provides cost-effective testing.

In one aspect, the present invention is thus directed to a method of detecting a mutation in a target nucleic acid molecule in sample, comprising the steps of: (i) contacting a first conjugate comprising a first nanoparticle and a first oligonucleotide analog, wherein the first oligonucleotide analog is a phosphorodiamidate morpholino oligo (PMO) or a derivative thereof that is covalently coupled to the first nanoparticle with an aliquot containing the target nucleic acid sequence, wherein the first oligonucleotide analog comprises a base sequence that is complementary to the unmutated sequence of the target nucleic acid, under conditions which allow the first conjugate and the target nucleic acid molecule to hybridize to each other, to form a first conjugate:target nucleic acid molecule complex; (ii) contacting a second conjugate comprising a second nanoparticle and a second oligonucleotide analog, wherein the second oligonucleotide analog is a phosphorodiamidate morpholino oligo (PMO) or a derivative thereof that is covalently coupled to the second nanoparticle with another aliquot containing the target nucleic acid sequence, wherein the second oligonucleotide analog comprises a base sequence that is complementary to the mutated sequence of the target nucleic acid and differs from the base sequence of the first oligonucleotide analog by at least one nucleobase and wherein the first and the second oligonucleotide analog have a sequence identity of at least 85%, under conditions which allow the second conjugate and the target nucleic acid molecule to hybridize to each other, to form a second conjugate:target nucleic acid molecule complex, and (iii) determining the melting temperatures $T_m$ of the complexes of (i) and (ii) and detecting whether said target nucleic acid molecule contains said mutation by comparing the $T_m$ of said complexes.

In a further aspect, the present relates to a kit comprising or consisting of a first and second conjugate, the first conjugate comprising a first nanoparticle and a first oligonucleotide analog, wherein the first oligonucleotide analog is a phosphorodiamidate morpholino oligo (PMO) or a derivative thereof that is covalently coupled to the first nanoparticle, and the second conjugate comprising a second nanoparticle and a second oligonucleotide analog, wherein the second oligonucleotide analog is a phosphorodiamidate morpholino oligo (PMO) or a derivative thereof that is covalently coupled to the second nanoparticle, wherein the first oligonucleotide analog differs from the second oligonucleotide analog by at least one nucleobase and wherein the first oligonucleotide analog has a sequence identity to the second oligonucleotide analog of at least 85%.

In a further aspect, the present invention relates to the use of a kit as described herein for the detection of mutation in a target nucleic acid molecule or for assigning a genotype to a target nucleic acid.

BRIEF DESCRIPTION OF THE DRAWINGS

The invention will be better understood with reference to the detailed description when considered in conjunction with the non-limiting examples and the accompanying drawings.

FIG. 16 shows the thermal cycler protocol for PCR amplification in warfarin genotyping.

FIG. 17 shows the $T_m$ values measured in the experiments according to FIG. 15 and the genotypes assigned based on the standard genotyping plots shown in FIG. 12.

DETAILED DESCRIPTION OF THE INVENTION

Figure 1:
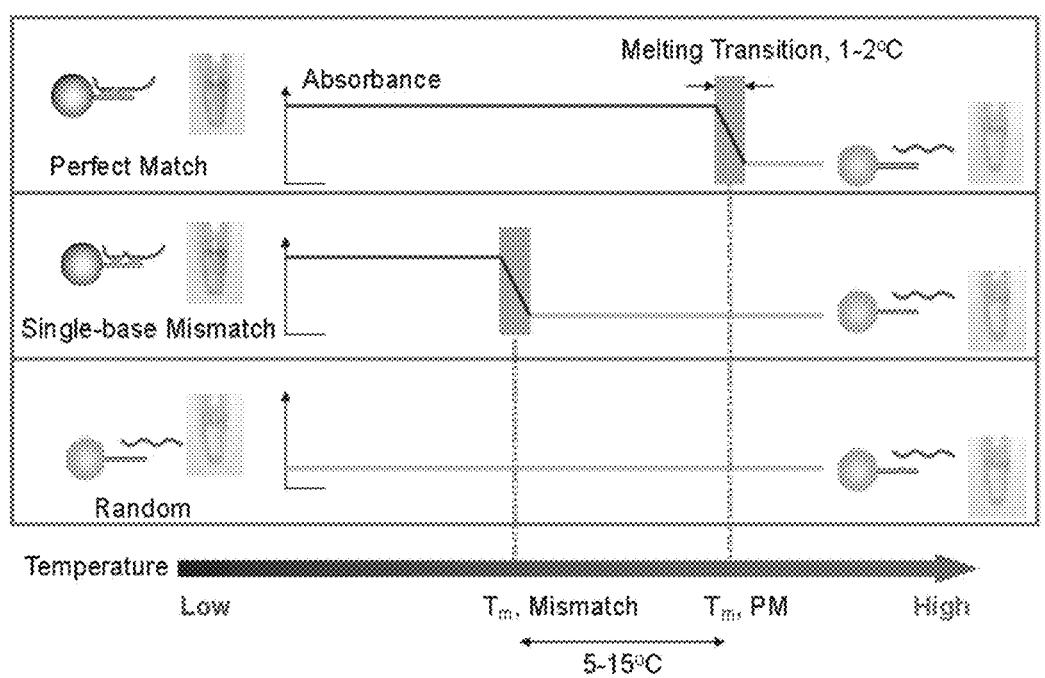
FIG. 1 shows a schematic illustration of the recognition of DNA targets by nanoprobes. When the target sequence is perfectly matched with the probe, the nanoparticles are stabilized in the presence of salt. As the temperature rises, the target/nanoprobe hybrids are dissociated at a temperature called the $T_m$, leading to aggregation of the nanoparticles and color change of the solution. A single-base mismatch results in a decrease in $T_m$ by 5-15° C. When the target sequence is random, the nanoprobe solution turns colorless at room temperature after 1-min incubation with salt.
Figure 2:
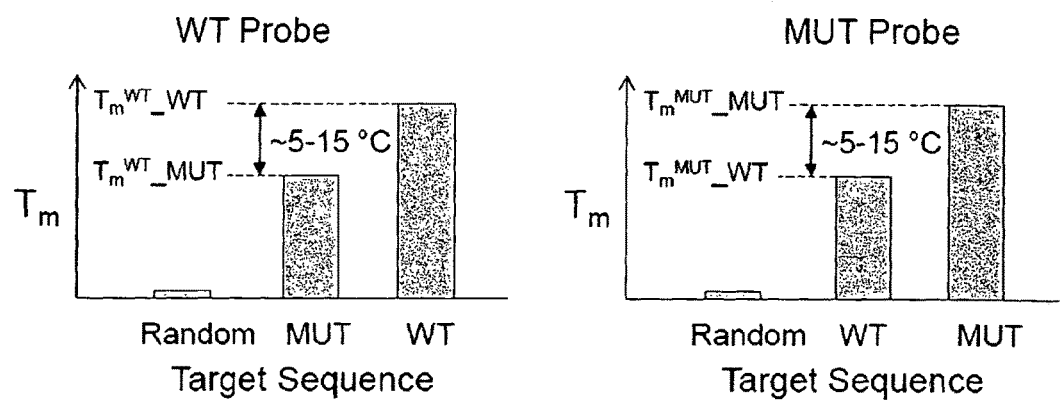
FIG. 2 shows the $T_m$ as a function of target sequence. A single-base mismatch of the nanoprobe and target sequences resulted in a decrease in $T_m$ by 5-15° C. When two sets of nanoprobes, WT and MUT probes, were employed, a pair of $T_m$ could be obtained for each target. The WT and the MUT targets were characterized by ($T_m^{WT}$_WT, $T_m^{MUT}$_WT) and ($T_m^{WT}$_MUT, $T_m^{MUT}$_MUT), respectively.
Figure 3:
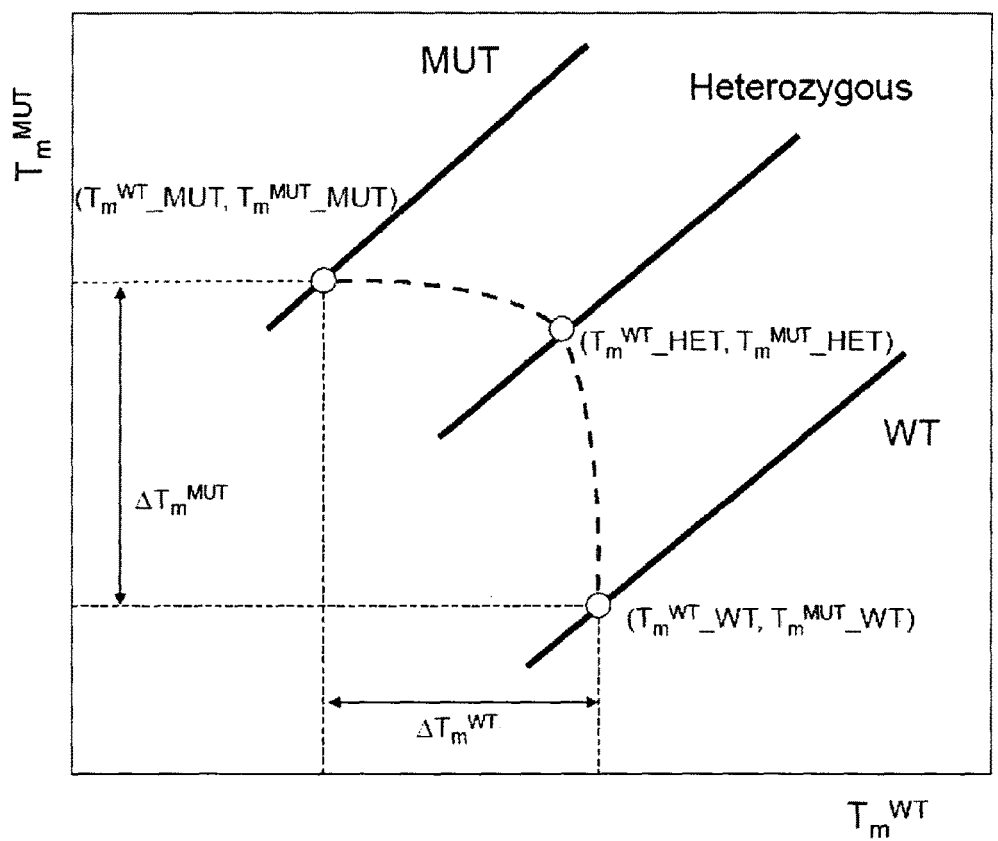
FIG. 3 shows a representative scatter plot of $T_m$ obtained by using WT and MUT nanoprobes. Depending on the target sequence, the data points ($T_m^{WT}$, $T_m^{MUT}$) lie in their specific linear regions (WT, MUT and Heterozygous regions), which were almost parallel to each other. The red dashed line represents the trace of data points corresponding to the MUT/WT ratio variation in heterogeneous samples.

The present inventors surprisingly found that two conjugates as described herein allows the robust and efficient detection of mutations, for example to identify SNPs (single-nucleotide polymorphism) in genomic DNA. Compared to detection systems known in the art (e.g. the ones disclosed in WO 2011/087456), the present system does not require the parallel detection of the same locus on a second control nucleic acid template molecule.

Thus, in a first aspect, the present invention is directed to a method for detecting a mutation in a target nucleic acid molecule in sample comprising the steps of:

(i) contacting a first conjugate comprising a first nanoparticle and a first oligonucleotide analog, wherein the first oligonucleotide analog is a phosphorodiamidate morpholino oligo (PMO) or a derivative thereof that is covalently coupled to the first nanoparticle with an aliquot of a sample suspected of containing the target nucleic acid sequence, wherein the first oligonucleotide analog comprises a base sequence that is complementary to the unmutated sequence of the target nucleic acid, under conditions which allow the first conjugate and the target nucleic acid molecule to hybridize to each other, to form a first conjugate:target nucleic acid molecule complex;

(ii) contacting a second conjugate comprising a second nanoparticle and a second oligonucleotide analog, wherein the second oligonucleotide analog is a phosphorodiamidate morpholino oligo (PMO) or a derivative thereof that is covalently coupled to the second nanoparticle with another aliquot of the sample suspected of containing the target nucleic acid sequence, wherein the second oligonucleotide analog comprises a base sequence that is complementary to the mutated sequence of the target nucleic acid and differs from the base sequence of the first oligonucleotide analog by at least one nucleobase and wherein the first and the second oligonucleotide analog have a sequence identity of at least 85%, under conditions which allow the second conjugate and the target nucleic acid molecule to hybridize to each other, to form a second conjugate:target nucleic acid molecule complex, and (iii) determining the melting temperatures $T_m$ of the complexes of (i) and (ii) and detecting whether said target nucleic acid molecule contains said mutation by comparing the $T_m$ of the complexes of (i) and (ii).

In various embodiments, the method further comprises the step of amplifying the target nucleic acid molecule by PCR previous to step (i).

In various embodiments, the sample is a heterogenous sample.

In various embodiments, the target nucleic acid molecule comprises the nucleotide sequence set forth in SEQ ID Nos. 3, 4, 13, 14, 15, 16, 17 or 18.

In a further aspect, the invention provides for the use of a composition as described herein for the detection of mutation in a target nucleic acid molecule or for assigning a genotype to a target nucleic acid.

In various embodiments of the invention, the target nucleic acid molecule differs from a corresponding wildtype nucleic acid molecule in 1, 2, 3, 4 or 5 nucleobases. In various other embodiments, the target nucleic acid molecule differs from a corresponding wildtype nucleic acid molecule by deletions of one or more nucleotides or insertions of one or more nucleotides.

In a further aspect, the invention relates to a kit comprising or consisting of a first and second conjugate, the first conjugate comprising a first nanoparticle and a first oligonucleotide analog, wherein the first oligonucleotide analog is a phosphorodiamidate morpholino oligo (PMO) or a derivative thereof that is covalently coupled to the first nanoparticle, and the second conjugate comprising a second nanoparticle and a second oligonucleotide analog, wherein the second oligonucleotide analog is a phosphorodiamidate morpholino oligo (PMO) or a derivative thereof that is covalently coupled to the second nanoparticle, wherein the first oligonucleotide analog differs from the second oligonucleotide analog by at least one nucleobase and wherein the first oligonucleotide analog has a sequence identity to the second oligonucleotide analog of at least 85%.

In various embodiments of the invention, the composition is useful for the detection of a mutation in at least one target nucleic acid molecule, wherein the first oligonucleotide analog comprises a sequence complimentary to the wildtype sequence of the target and the second oligonucleotide analog comprises a sequence complimentary to the mutated sequence of the target or vice versa. The wildtype sequence and mutated sequence may differ by one or more nucleobases, preferably differ by 1, 2, 3, 4 or 5 nucleobases. Apart from such point mutations, the two sequences may also differ by deletions of one or more nucleotides or insertions of one or more nucleotides.

The detection principle is based on the fact that perfectly complementary probe:target complexes have a higher $T_m$ than complexes that are not fully complementary. "Complementarity", as used herein, relates to Watson-Crick base pairing, with perfect complementarity meaning that all bases in the probe Watson-Crick base pair with the corresponding bases in the target. Accordingly, a genotype can be assigned to the target nucleic acid based on the melting transition temperature value measured. In case the probe specific for the mutated sequences forms a complex with a higher $T_m$ than the probe specific for the wildtype sequence, the mutation is present and a mutated genotype can be assigned to the target sequence. In contrast, in case the probe specific for the wildtype sequences forms a complex with a higher $T_m$ than the probe specific for the mutated sequence, the mutation is not present and a wildtype genotype can be assigned to the target sequence.

In various embodiments of the invention, the nanoparticle is a metal nanoparticle. Preferably the metal is a noble metal. The noble metal may be selected from the group consisting of silver, gold, platinum, palladium, ruthenium, osmium, iridium and mixtures thereof. In various preferred embodiments, the metal is gold.

In various embodiments of the invention, the diameter of the nanoparticle is in the range of about 1 nm to about 100 nm.

In various embodiments of the invention, a monomeric unit of the phosphorodiamidate morpholino oligo or derivative thereof is represented by formula (I)

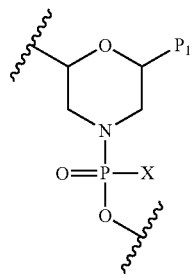

(I)

wherein $P_1$ is a purine or pyrimidine base that forms Watson-Crick base pairs with another purine or pyrimidine base, preferably a nucleobase; and X is $NH_2$, NHR, or $NR_2$, wherein R is C1-C6 alkyl, preferably R is methyl. In various embodiments, the purine or pyrimidine base is a nucleobase selected from the group consisting of adenine (A), cytosine (C), guanine (G), thymine (T) and uracil (U). In various other embodiments, the nucleobase is selected from derivatives of the afore-mentioned nucleobases, such as 5-methylcytosine (m5C), pseudouridine (Ψ), dihydrouridine (D), inosine (I), and 7-methylguanosine (m7G) as well as xanthine and hypoxanthine.

In various embodiments of the invention, the first and second oligonucleotide analogs comprise about 15 to about 35 monomeric units.

In one embodiment of the invention, the first oligonucleotide analog comprises the base sequence set forth in SEQ ID NO:1 and the second oligonucleotide comprises the base sequence set forth in SEQ ID NO:2.

In another embodiment of the invention, the first oligonucleotide comprises the base sequence set forth in SEQ ID NO:7 and the second oligonucleotide comprises the base sequence set forth in SEQ ID NO:8.

In another embodiment of the invention, the first oligonucleotide comprises the base sequence set forth in SEQ ID NO:9 and the second oligonucleotide comprises the base sequence set forth in SEQ ID NO:10.

In another embodiment of the invention, the first oligonucleotide comprises the base sequence set forth in SEQ ID NO:11 and the second oligonucleotide comprises the base sequence set forth in SEQ ID NO:12.

In all above-described embodiments, the backbone of the oligonucleotides is the above-defined phosphorodiamidate morpholino backbone.

In various embodiments of the invention, the at least one oligonucleotide analog is covalently coupled to the nanoparticle via a functional group, with the functional group optionally being part of a linker molecule. Preferably, the functional group comprises a thiol group.

In various embodiments of the invention, the kit further comprises PCR primers. In one embodiment of the invention, the kit is used in the genotyping of a p53 gene and the primers comprise or consist of the nucleotide sequences set forth in SEQ ID NO:5 and SEQ ID NO:6. In various other embodiments of the invention, the kit is used in determining warfarin sensitivity wherein the primers pairs are selected from: SEQ ID NO:19 and SEQ ID NO:20; SEQ ID NO:21 and SEQ ID NO:22; or SEQ ID NO:23 and SEQ ID NO:24.

In a still further aspect of the invention, the kits as described herein are used for the detection of mutation in a target nucleic acid molecule or for assigning a genotype to a target nucleic acid.

The term "composition", as used herein, relates to a mixture of at least two different types of compounds, elements, molecules and/or conjugates. Said mixture may be a dry mixture containing the at least two different types of compounds, elements, molecules and/or conjugates in solid forms or said at least two different types of compounds, elements, molecules and/or conjugates may be dissolved in a suitable solvent.

The term "conjugate," as used herein, refers to a molecule comprising two or more chemical groups (e.g., peptides, carbohydrates, nanoparticles, small molecules, or nucleic acid molecules) that are linked. The two or more groups are chemically linked using any suitable chemical bond (e.g., covalent bond). Suitable chemical bonds are well known in the art and include disulfide bonds, acid labile bonds, photolabile bonds, peptidase labile bonds (e.g. peptide bonds), thioether, and esterase labile bonds. In a preferred embodiment of the invention, the chemical bond comprises a thiol group.

The term "nanoparticle", as used herein, relates to a particle that is defined as a small object that behaves as a whole unit with respect to its transport and properties. In general, particles are classified according to their diameter. Nanoparticles are between 1 and 100 nanometers in size. Preferably, nanoparticles of the invention are noble metal nanoparticles, more preferably said particles are selected from the group consisting of silver, gold, platinum, palladium, ruthenium, osmium, iridium and mixtures thereof. In various preferred embodiments, the nanoparticles are gold nanoparticles.

The terms "nucleic acid molecule", "nucleic acid sequence" or "oligonucleotide", as used herein, relate to any nucleic acid molecule in any possible configuration, including single-stranded, double-stranded configurations or a combination thereof. Isolated oligonucleotides include for instance phosphorodiamidate morpholino oligo (PMO), DNA molecules, RNA molecules and analogues of DNA or RNA comprising modified backbones, internucleotide linkages, sugars or bases. DNA or RNA may be of genomic or synthetic origin. Such nucleic acids include but are not limited to mRNA, cRNA, synthetic RNA, genomic DNA, cDNA, synthetic DNA and DNA/RNA hybrid. As described above, oligonucleotides are either synthetic constructs or nucleic acids separated from other cellular components with which it may naturally occur including cellular debris or are synthesized using known methods. The resulting nucleic acids are preferably 70, 80 or 90% pure, preferably at least 95 or 98% pure nucleic acid containing less than 30% contaminants, preferably less than 20 or 10% and most preferably less than 5 or 2% contaminants that cannot be identified as the nucleic acid as described herein. The term "nucleic acid molecule/sequence" further refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Nucleosides may also contain nucleobases such as 5-methylcytosine (m5C), pseudouridine (Ψ), dihydrouridine (D), inosine (I), and 7-methylguanosine (m7G) as well as xanthine and hypoxanthine Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

Various nucleotide analogues are known and can be incorporated as part of, or replaced in its entirety, the isolated oligonucleotide of the present invention. A nucleotide analogue as defined herein is a nucleotide modified at the backbone, internucleotide linkage, sugar or base moiety. Modifications at the backbone or internucleotide linkage moiety include peptide nucleic acid (PNA) and substitution of the phosphate group by phosphorothioate. Modifications at the sugar moiety include the incorporation of the six membered morpholine ring. Modifications of the base moiety include alterations of A, T/U, G and C. Modifications of these different moieties can be applied on the same nucleotide in concert. Incorporation of nucleotide analogues within the isolated oligonucleotide can lead to improved nuclease resistance. Preferably, nucleic acid molecules of the present invention have at least one modification at N2-position of a given guanine base.

The term "oligonucleotide analog" refers to an oligonucleotide having modified sugar moieties. The oligonucleotide analogs of the invention have preferably a length of at most 50, 45, 40, 35, 30, 25, 20, 15 or 10 bases. Compared to naturally occurring RNA or DNA, in such modified oligonucleotides the five membered sugar ring is replaced by a six membered morpholine ring. Such oligonucleotide molecules are known in the art as phosphorodiamidate morpholino oligo (PMO) or morpholino. Derivatives of phosphorodiamidate morpholino oligos comprise molecules wherein at least one of hydrogen atoms that are linked to the carbon and/or nitrogen atoms of the morpholine ring are replaced by a substituent. Preferably, such substituent is an organic moiety.

The term "covalently coupled", as used herein, relates to a chemical bond that involves the sharing of electron pairs between atoms. The stable balance of attractive and repulsive forces between atoms when they share electrons is known as covalent bonding.

"At least one", as used herein, relates to one or more, in particular 1, 2, 3, 4, 5, 6, 7, 8, 9, 10 or more.

The term "nucleobase" relates to nitrogen-containing biological compounds (nitrogenous bases) found within nucleotides—the basic building blocks of deoxyribonucleic acid (DNA) and ribonucleic acid (RNA). Often the nucleobases are also called bases and their ability to form base-pairs and to stack upon one another lead directly to the helical structure of DNA and to the secondary structures of RNA.

The term "sequence", as used herein, relates to the primary nucleotide sequence of nucleic acid molecules.

As used herein, "sequence identity" or "identity" in the context of two nucleic acid or peptide sequences makes reference to the residues in the two sequences that are the same position when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. In various embodiments of the invention, the sequence identity of the first oligonucleotide analog and the second oligonucleotide analog is at least 85%, 90%, 95%, 98% or 99%.

The term "metal", as used herein, relates to an element, compound, or alloy that is typically hard, opaque, shiny, and features good electrical and thermal conductivity. Noble metals are resistant to corrosion and oxidation in moist air, unlike most base metals. They tend to be precious, often due to their rarity in the Earth's crust. The noble metals are most commonly considered to be ruthenium, rhodium, palladium, silver, osmium, iridium, platinum, and gold.

The term "monomeric unit" in relation to phosphorodiamidate morpholino oligo (PMO), as used herein, refers to one given nucleoside within the oligomeric PMO molecule. Such "monomeric unit" is represented by the formula (I) of this invention (cf. paragraph [00038]).

"Watson-Crick base pairs", as used herein relates to the intramolecular base pairs that occur within single-stranded nucleic acids or between at least two different nucleic acid molecules. The standard or canonical Watson-Crick base pairs are A-U(T) and G-C.

By the term "functional group", as used herein, any chemical molecule or group is meant that can be attached to the oligonucleotide or to the nanoparticle including protecting groups, fluorescent or otherwise detectable groups, tags, and/or highly reactive moieties. Optionally, such functional group may be located on a linker molecule. The linker molecule may comprise more than one functional group, so that the linker molecule can connect different oligonucleotides and nanoparticles.

The term "detection", as used herein, relates to quantitatively or qualitatively identifying a mutation in a nucleic acid molecule. In preferred embodiments of the invention, the nucleic acid molecule is derived from genomic DNA. In various other embodiments, the genomic DNA is "heterogeneous". This means that a given genetic diploid locus in the genomic DNA occurs in two different variations. Such genomic DNA, which contains at a gene locus two different alleles of a gene, is also known as heterozygous.

The term "contacting", as used herein, refers generally to providing access of one component, reagent, analyte or sample to another. For example, contacting can involve mixing a solution comprising a conjugate of the invention with a sample comprising a target nucleic acid. Optionally, contacting can involve mixing a solution comprising a conjugate of the invention with genomic DNA that previously has been amplified by PCR. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples.

In various embodiments of the invention, the sample is a biological sample, for example a body fluid, cell or tissue sample. Body fluids comprise, but are not limited to blood, blood plasma, blood serum, breast milk, cerebrospinal fluid, cerumen (earwax), endolymph and perilymph, gastric juice, mucus (including nasal drainage and phlegm), peritoneal fluid, pleural fluid, saliva, sebum (skin oil), semen, sweat, tears, vaginal secretion, nipple aspirate fluid, vomit and urine. The cell or tissue sample may comprise material originated from any part of the body such as connective tissue, muscle tissue, nervous tissue, and epithelial tissue. The term "obtaining a sample", as used herein, relates to different methods known in the art that comprise, but not limited to, biopsy, sentinel node biopsy or removal of blood, bone marrow, sputum or bronchial fluids.

The term "target nucleic acid molecule", as used herein, relates to a nucleic acid molecule whose nucleotide sequence has to be determined. The target nucleic acid molecule may be a whole chromosome or, optionally, a given gene of said chromosome or only a part of an intron or exon of the given gene. Preferably, one specific genetic locus on the target nucleic acid molecule is determined by the method of the invention. However, it is also possible that two or more different loci are determined within one gene or chromosome. Such determination may be realized by using further conjugates that are complementary to the mutations assumed to be present on the further loci. Alternatively, one specific genetic locus may also be tested for the presence of different mutations by using conjugates that are perfectly complementary to each of the assumed mutations. In this context, "wildtype sequence" relates to a nucleotide sequence that is different from a nucleotide sequence that contains one or more mutations. This means that the term "wildtype sequence" may refer to the nucleotide or nucleotide sequence that is found in the majority of individuals. In this context, majority can be understood as the genetic variant with the highest frequency in a representative group of individuals. Such representative group may represent the whole humankind, or may be a group representing individuals that have been selected based on their age, gender, weight, family's disease history and/or other parameters. However, the term "wildtype sequence" may also refer to the genotype of the typical form of a species as it occurs in nature and that is not related to a pathological condition. In the context of a specific genetic locus, the term "mutation" or "mutated", as used herein, relates to any nucleotide or nucleotide sequence that is different from the wildtype sequence.

"Complementary" sequences, as used herein, refer to sequences in which antiparallel alignment juxtaposes A residues on one strand with T or U residues and G with C residues on the other strand such that A:T, A:U, and G:C hydrogen-bonded base pairs can form. These are the standard "Watson-Crick" base pairs occurring in the vast majority of DNA and RNA hybrids in vivo. As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. "Complementary" sequences can also include, or be formed entirely from, non-Watson-Crick base pairs and/or base pairs formed from non-natural and modified nucleotides, in as far as the requirements with respect to their ability to hybridize are fulfilled.

The terms "complementary", "fully complementary" and "substantially complementary" herein may be used with respect to the base matching between the sense strand and the antisense strand of a double-stranded nucleic acid hybrid. A "fully complementary" hybrid has every nucleotide on one strand base paired with its juxtaposed counterpart on the opposite strand. In a "substantially complementary" hybrid, the two strands can be fully complementary, or they can include one or more, but preferably not more than 30, 20, or 10 mismatched base pairs upon hybridization, while retaining the ability to hybridize under the conditions used in the methods described herein. In a preferred embodiment of the invention, the compared nucleotide sequences are fully complementary.

The term "complex", as used herein, relates to a molecule wherein a conjugate of the invention binds to the target nucleic acid molecule. Said binding is based on the hybridization of the complementary nucleotide sequences.

The term "conditions that allow hybridization" relates to specific buffer conditions, such as salt and detergent concentrations, and temperature conditions that allow the binding of two or more different nucleic acid molecules to each other to form "Watson-Crick" or non-Watson-Crick base pairs. Conditions that allow hybridization of two or more nucleic acid molecules dependent strongly on the length of the complementary sequence and on their specific sequence. Such binding conditions are known in the art (Gilmartin, P M (1996) Nucleic Acid Hybridization: Essential Data, Wiley; 1 edition).

The term "$T_m$" or "melting temperature", as used herein, is defined as the temperature at which half of the nucleic acid strands are in the random coil or single-stranded state. The melting temperature depends on the length of the nucleic acid molecule and its specific nucleotide sequence.

In the context of genotype, the terms "assign" and "determine", relate to the identification of a genotype of a given genetic locus.

The term "deletion", as used herein, relates to a mutation in which a part of a chromosome or a sequence of DNA or RNA is missing. Deletion is the loss of genetic material. Any number of nucleotides can be deleted, from a single base to an entire piece of chromosome. Deletions can be caused by errors in chromosomal crossover during meiosis. In contrast, the term "insertion", as used herein, refers to the addition of one or more nucleotide bases or base pairs into an RNA or DNA sequence. This can often happen in microsatellite regions due to the DNA polymerase slipping. Insertions can be anywhere in size from one base pair incorrectly inserted into a DNA sequence to a section of one chromosome inserted into another.

The term "PCR primer", as used herein, relates to a nucleic acid oligomer that serves as a starting point for DNA synthesis and hybridizes with the flanking regions of the nucleic acid sequence that should be amplified. It is required for DNA replication because the enzymes that catalyze the amplification process, DNA polymerases, can only add new nucleotides to an existing strand of DNA. The polymerase starts replication at the 3'-end of the primer, and copies the opposite strand. PCR primers have usually a length of at least 10 nucleotides. Preferably, the length of PCR primers of the invention is between 20 and 35 nucleotides.

The target nucleic acid molecule obtained from a sample may be amplified prior to the step of contacting it with the conjugates of the invention. Such amplification may be carried out by utilization of the polymerase chain reaction (PCR) technology. Different types of PCR technology may be used to amplify the target nucleic acid molecule. Such types of PCR technology include, but are not limited to allele-specific PCR, assembly PCR, asymmetric PCR, dial-out PCR, digital PCR, helicase-dependent amplification, hot start PCR, intersequence-specific PCR (ISSR), inverse PCR, ligation-mediated PCR, methylation-specific PCR (MSP), miniprimer PCR, multiplex ligation-dependent probe amplification (MLPA), multiplex-PCR, nanoparticle-assisted PCR (nanoPCR), nested PCR, overlap-extension PCR or splicing by overlap extension (SOEing), PAN-AC, reverse transcription PCR (RT-PCR), solid phase PCR, thermal asymmetric interlaced PCR (TAIL-PCR), touchdown PCR (step-down PCR), universal fast walking or transcription-mediated amplification (TMA). Such techniques are well-known in the art (McPherson, M J and Moller, S G (2000) PCR (Basics), Springer-Verlag Telos; first edition).

EXAMPLES

Materials and Methods
Preparation of the Nanoprobes
The preparation of the nanoprobes used in this study is similar to that reported by Zu et al. (Zu, Y et al. (2011) Small, 7, 306-310). Briefly, the MORs modified with disulfide amide at the 3' terminal (Gene Tools, LLC) were treated with dithiothreitol, and then purified by using an NAP-5 column (GE Healthcare). Gold nanoparticles (40 nm-diameter, ~0.1 nM) were mixed with ~2 µM of thiolated MORs and 10 mM of phosphate buffer (pH 7.5), and allowed to incubate at room temperature for 2 h. Next, the MOR-nanoparticle conjugates were washed 5 times with a phosphate buffer solution (5 mM, pH 7.5) and centrifuged to remove the unreacted MORs. The conjugates can be used immediately as nanoprobes or stored in 4° C. refrigerator until use. The nanoprobes are stable for at least 6 months when stored at 4° C. Before use, the nanoprobe solutions need to be uniformly dispersed by vortexing.

Genomic DNA (gDNA) Extraction
Extraction of gDNA from cultured cells was performed with the use of the Wizard® SV Genomic DNA Purification System (Promega), according to the manufacturer's instructions. Quantity (ng/µl) and quality (A260/A280 ratio) of the gDNA samples were checked by measuring the absorbance using Nanodrop 1000 (Thermo Scientific). For MCF-7 and MADMB-231 gDNA samples, the ratios of absorbances at 260 nm and 280 nm (A260/A280 ratios) were 1.78 and 1.81, respectively.

In the warfarin genotyping study, gDNA extraction from the human cheek swab was performed with the use of the following commercial kits, the Wizard® SV Genomic DNA Purification System (Promega), Gentra Puregene DNA Extraction Kit (Qiagen), or the QIAamp DNA Investigator Kit (Qiagen), according to the manufacturer's instructions. A260/A280 ratios of the samples varied from 1.62 to 1.95.

PCR
PCR for the amplification of the target sequence containing codon 280 in exon 8 of the p53 gene was performed by using primers set forth in SEQ ID Nos. 1-6. The solution with a final volume of 25 µL contained ~10 ng of gDNA, 12.5 µL of Fermentas master mix (2×), and 1 µM of each primer. For the mutation detection in the background of wildtype DNA, the total amount of gDNA in the PCR mixture was increased to 100 ng so that the quantity of the low-level mutant template was sufficient for amplification. PCR cycling was performed on the PTC-200 DNA Engine (Bio-Rad) according to the following conditions: one cycle of 95° C. for 2 min, 40 cycles of 95° C. for 20 sec, 55° C. for 30 sec, and 72° C. for 30 sec. The success of the PCR to produce 319-bp amplicons was verified by running a 5-µL aliquot of the PCR products on a 1.5% agarose gel containing SafeView. To generate ssDNA targets, lambda-exonuclease digestion strategy was employed (Higuchi, R G and Ochman, H (1989) Nucleic Acids Res, 17, 5865-5865). Phosphate-labeled reverse primers were used in PCR. 20 µL of the PCR products were incubated with 10 units of lambda-exonuclease (Fermentas) for 10 mM, followed by deactivation of the enzyme at 80° C. for 10 min.

aPCR (Asymmetric Polymerase Chain Reaction)
In warfarin sensitivity test kit, aPCR was used to produce ssDNA targets. PCR solution with a final volume of 25 µL contained ~10 ng of gDNA, 12.5 µL of master mix (Fermentas or Promega, 2×), 1 µM of the forward primer, and 100 nM of the reverse primer. PCR cycling was performed on the PTC-200 DNA Engine (Bio-Rad) (cycling parameters are shown in FIG. 16). The success of the PCR in producing specifically sized amplicons was verified by running a 5 µL aliquot of the PCR products on a 1.5% agarose gel stained with SafeView™ dye.

$T_m$ Measurements
The synthetic targets or the ssDNA amplicons were mixed with the specific WT and MUT nanoprobes, respectively. Next, the $T_m$ values of the target-probe hybrids were measured with the thermal cycler. The temperature was increased from 30° C. at an interval of 1.0° C. At each temperature, the solution was allowed to incubate for 1 min prior to the color visualization or recording with a camera. When a clear color change from red to light grey was observed, the temperature was recorded as $T_m$.

Genotype Assignment
The ($T_m^{WT}$-$T_m^{MUT}$) scatter plots obtained with the synthetic DNA targets (FIG. 5 and FIG. 12 for p53 and warfarin testing, respectively) were used as the standard genotyping diagrams. The experimental data point ($T_m^{WT}$, $T_m^{MUT}$) is plotted in the specific diagram, and its location is used to determine the genotype of the sample. The data points are usually grouped along one of the three genotype regions. The samples with data points locating below the WT standard region should be assigned as WT, while the samples with data points locating above the MUT standard region should be assigned as MUT.

Figure 5:
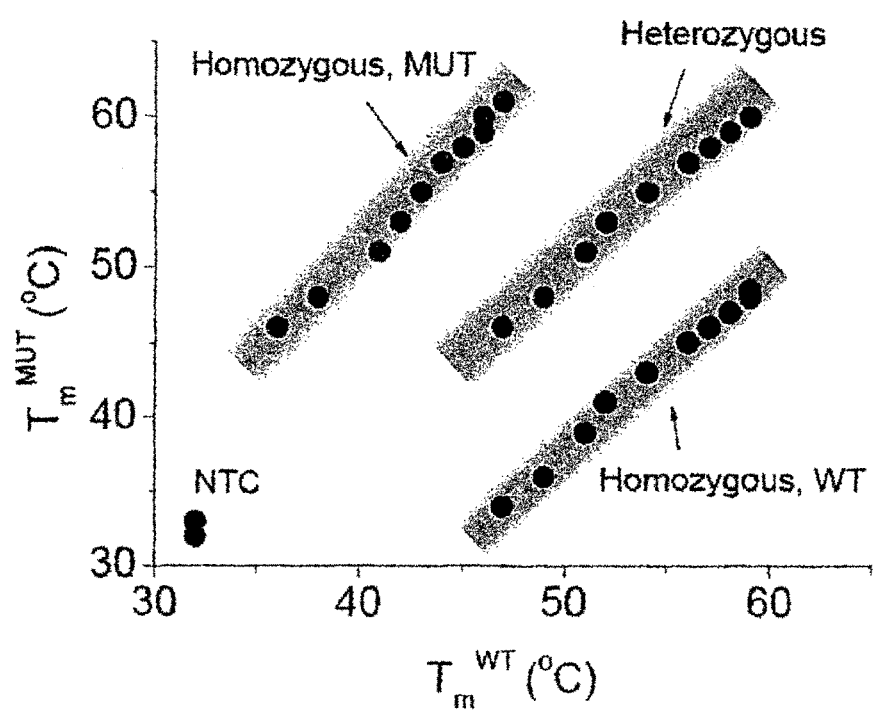
FIG. 5 shows a scatter plot of $T_m$ WT and $T_m$ MUT obtained by using p53 WT and MUT nanoprobes and synthetic DNA targets.

Somatic Mutation Determination
According to FIG. 5, the value of $T_m^{WT}$ was used to determine the lower limit of $T_m^{MUT}$ (i.e., $T_m^{MUT}$_WT, a value obtained for 100% of WT targets). If the measured value of $T_m^{MUT}$ was higher (≥2° C.) than the lower limit, the sample should be assigned as somatic mutation.

Example 1: Analysis of the p53 Gene

To demonstrate the dual-nanoprobe genotyping method, genomic DNA (gDNA) from two human cell lines, MCF-7 and MDA-MB-231, was extracted and analyzed to determine the mutation state of the p53 gene, codon 280. The p53 gene is known as a tumor suppressor gene that codes for the p53 protein, which inhibits the development and growth of tumors. Mutations of the gene are common in diverse types of human cancer (Hollstein, M et al. (1992) Science, 253, 49-53). The codon 280 G>A homozygous mutation occurs in the human breast cancer cell line MDA-MB-231, while the p53 gene of the cell line MCF-7 is wild-type (Bartek, J (1990) Oncogene, 5, 893-899).

The MOR sequences used to prepare the WT and MUT nanoprobes are set forth by SEQ ID Nos. 1-6. Both the WT and MUT nanoprobes were stably dispersed in 5 mM of phosphate buffer solutions (pH ~7.5). Clear color change was observed when 50 mM of NaCl was added to the nanoprobe solution. The behavior was similar to that reported previously, although the MOR sequences were different (Zu, Y et al. (2011) Small, 7, 306-310).

Figure 4:
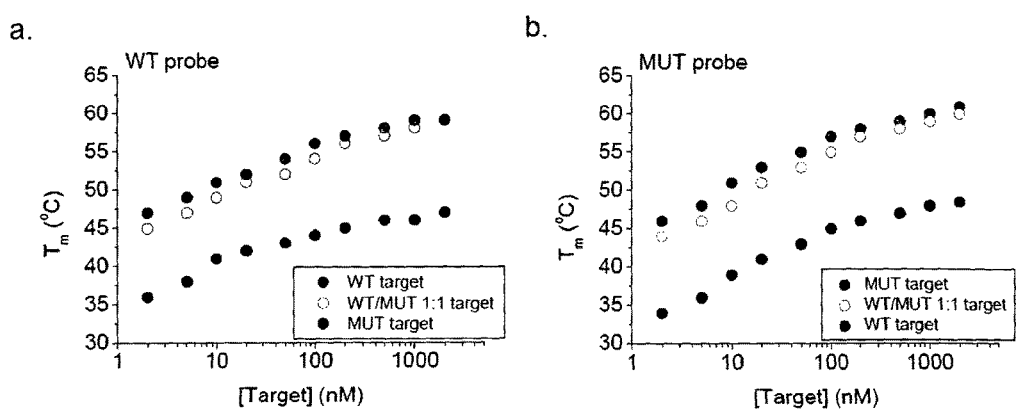
FIG. 4 shows $T_m$ values as a function of the synthetic target concentration for (a) a p53 WT nanoprobe and (b) a p53 MUT nanoprobe. Error of $T_m$ measurement=±1° C.

Synthetic 101-nucleotide single-stranded DNA (ssDNA) targets were used to study the ability of the nanoprobes in sequence discrimination. The targets represented the WT and MUT sequences of the p53 gene segments, respectively. The single-base variation of G>A was located in the intermediate site of the sequences. In the presence of ≥2 nM of either the WT or MUT targets, both of the WT and MUT nanoprobes were stabilized and no color change occurred after incubation with 50 mM of NaCl. With increasing temperature, the $T_m$ values of the nanoprobe-target hybrids were obtained based on the change in solution color. FIG. 4 shows the $T_m$ values as a function of the target quantity. At each given target concentration, the single-base-mismatch induced $T_m$ differences for the WT and MUT probes; $\Delta T_m^{WT}$ and $\Delta T_m^{MUT}$ varied from 10° C. to 12° C. The responses of the nanoprobes toward heterozygous samples (obtained by mixing the WT and MUT targets at a ratio of 1:1) are also shown in FIG. 4.

A scatter plot of ($T_m^{WT}$-$T_m^{MUT}$) for WT, MUT and WT/MUT=1:1 (representing the heterozygous genotype) targets is shown in FIG. 5. As the target concentration was varied over a relatively broad range from 5 nM to 500 nM, 3 groups of data points corresponding to 3 types of the target sequences were found along their specific linear regions, and were distinctly separated from each other. The results demonstrated that the dual probe assay was robust, and works even when the target quantity varied significantly. In the analysis of PCR products, the target concentration was determined by the template quantity and the polymerase reaction yield. The ability to determine the genotype of a sample without stringent controls over the assay conditions is highly desirable.

Figure 6:
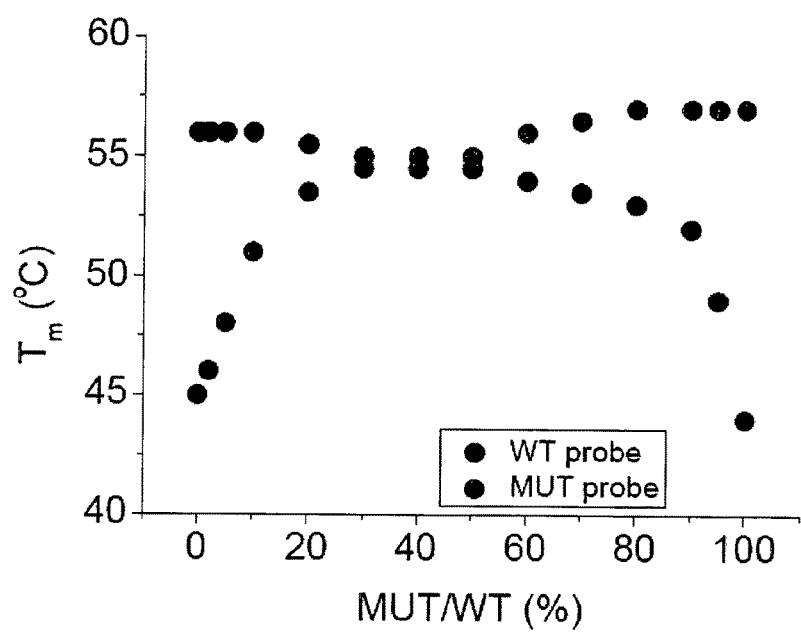
FIG. 6 shows $T_m$ values obtained by using p53 WT and MUT probes as the MUT/WT sequence ratio of synthetic DNA was varied. Error of $T_m$ measurement=±1° C.

To examine the mutation detection sensitivity, a series of heterozygous samples with a total concentration of 100 nM was analyzed using the dual-nanoprobe method. FIG. 6 shows the $T_m$ values as a function of the MUT/WT ratio. When the ratio was less than 20%, the values of $T_m^{WT}$ were identical to $T_m^{WT}$_WT. On the other hand, the values of $T_m^{MUT}$ were well above $T_m^{MUT}$_WT as long as the ratio was larger than 2%. Therefore, for a highly heterogeneous sample, the value of $T_m^{WT}$ could serve as $T_m^{MUT}$_WT and be used to determine the corresponding value of $T_m^{MUT}$_WT according to FIG. 5. The presence of the mutant sequence resulted in the higher value of $T_m^{MUT}$ as compared to $T_m^{MUT}$_WT.

Example 2: Genotyping with the Dual-Nanoprobe Method

Figure 7:
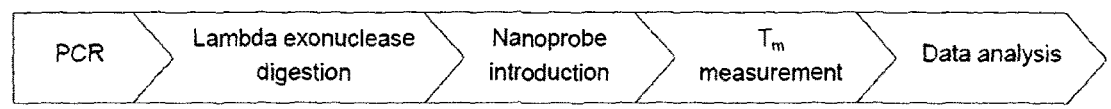
FIG. 7 shows a workflow of the nanoprobe-based genetic testing for the p53 gene analysis.
Figure 8:
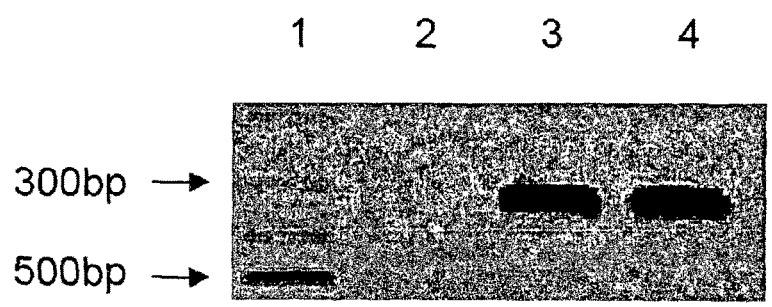
FIG. 8 shows the results of a PCR amplification of 319-bp DNA fragments of the p53 gene.

The experimental workflow for analyzing the codon 280 genotype of human p53 gene is shown in FIG. 7. The gDNA samples were extracted from two cell lines with known genotypes, i.e., MCF-7 (wild-type) and MDA-MB-231 (homozygous mutation). The heterozygous samples were obtained by mixing (at a 1:1 ratio) the gDNA samples extracted from the MCF-7 and MASMB-231 cell lines. Using these gDNA samples as templates, DNA fragments of 319 by were produced by PCR. The reverse primer for the PCR was phosphate-labeled. Gel electrophoresis showed the specific amplification of the desired fragments (FIG. 8).

Figure 9:
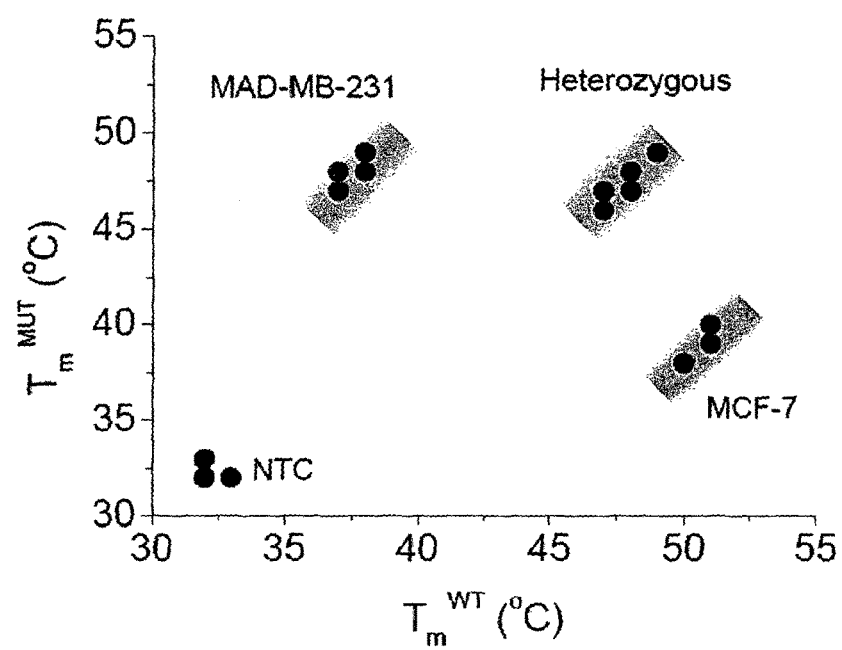
FIG. 9 shows a scatter plot for genotyping of the p53 gene, codon 280 G>A. The gDNA samples were extracted from cell lines MCF-7 and MDA-MB-230. The heterozygous sample was a 1:1 mixture of WT and MUT gDNA. The data for each sample were obtained from six independent assays (some data points overlapped with one another).

Following PCR, ssDNA targets were obtained by lambda-exonuclease digestion of the phosphate-labeled strands of the amplicons (Higuchi, R G and Ochman, H (1989) Nucleic Acids Res, 17, 5865-5865). Next, two aliquots of the ssDNA products were mixed with the WT and MUT probes, respectively, and $T_m^{WT}$ and $T_m^{MUT}$ were measured. No post-PCR clean-up was conducted. FIG. 9 shows the scatter plot for genotyping of the cell line samples. All the genotypes were determined correctly and unambiguously.

It is noted that the assay worked well in the presence of the primers, polymerase and lambda exonuclease, suggesting the weak interactions of the nanoprobes with these species. The high specificity of the nanoprobes in DNA sequence recognition ruled out the possibility of primer attachment. Because of the nonionic and hydrophilic nature of MORs, the nanoprobes also showed low affinity to proteins. These features made the nanoprobes robust in the analysis of complicated samples, greatly simplifying the assay workflow.

Example 3: Sensitivity in the Analysis of Highly Heterogeneous Specimens

Previous studies suggested that the unique features of the nanoprobes allowed sensitive detection of the low-level mutant (Zu, Y et al. (2011) Small, 7, 306-310). Herein the dual-nanoprobe assay was used in the analysis of highly heterogeneous specimens.

Figure 10:
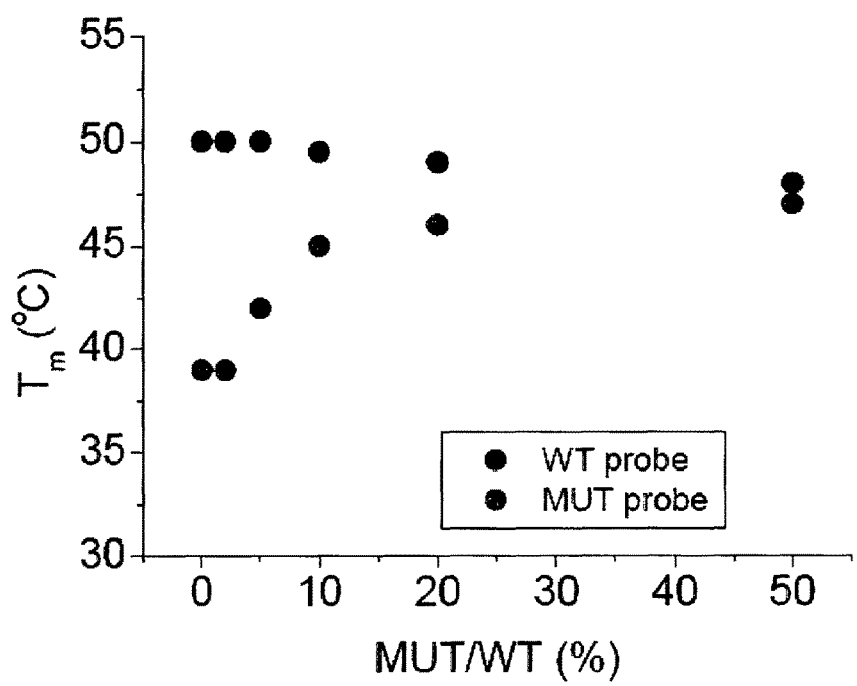
FIG. 10 shows $T_m$ values obtained by using p53 WT and MUT probes as the MUT/WT sequence ratio of gDNA was varied.

A series of heterogeneous samples were prepared by mixing the gDNA extracted from MDB-MB-231 and MCF-7 cell lines with different ratios. FIG. 10 shows the values of $T_m^{WT}$ and $T_m^{MUT}$ as a function of the gDNA ratio. Similar to the results obtained by using synthetic DNA samples (FIG. 6), the value of $T_m^{WT}$ could be used to determine the lower limit of $T_m^{MUT}$ (i.e., $T_m^{MUT}$_WT, a value obtained for 100% WT target). If the measured value of $T_m^{MUT}$ was obviously higher (2° C.) than the lower limit, somatic mutations are detected. Based on this criterion, the sensitivity of the dual-nanoprobe assay for the p53 mutation detection was ~5%. The assay was more sensitive than Sanger sequencing (sensitivity ~20%), and comparable to some of the PCR enrichment technologies (Higuchi, R G and Ochman, H (1989) Nucleic Acids Res, 17, 5865-5865). As an end-point detection method, the assay was compatible with the PCR-based target-enrichment strategies. Higher sensitivity would be expected when the dual-nanoprobe assay was used in conjunction with allele-specific PCR or clamping PCR.

Example 4: Development of Warfarin Sensitivity Test Kit

In this study, 3 pairs of WT and MUT nanoprobes were employed to gauge the 3 SNPs associated with warfarin sensitivity (SEQ ID Nos. 7-12). The nanoprobes can be stably dispersed in 5 mM of phosphate buffer solution (pH ~7.5). However, clear color change occurred after 1-min incubation with 50 mM of NaCl.

Figure 11:
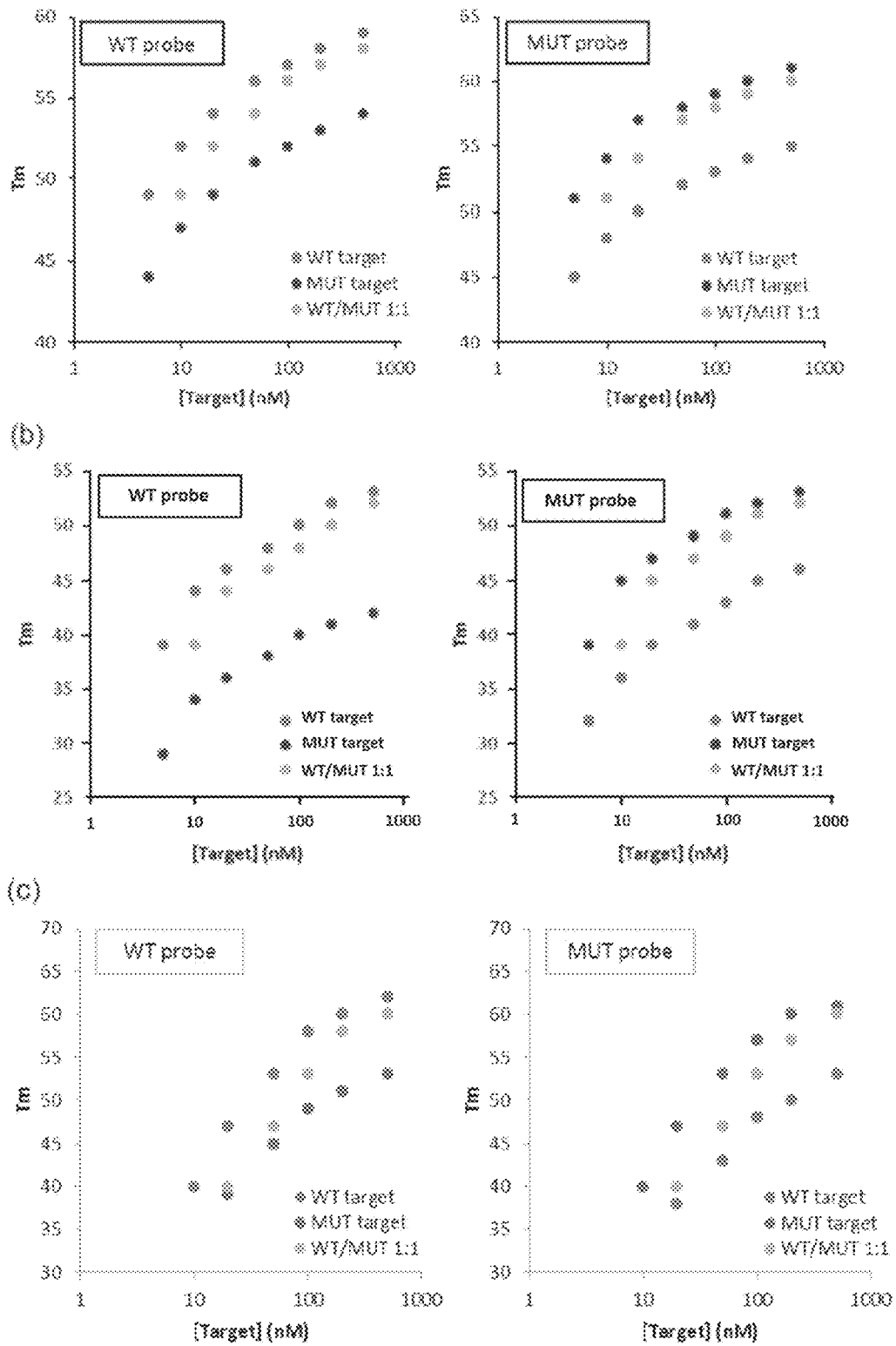
FIG. 11 shows the $T_m$ vas a function of the synthetic target concentration of WT and MUT probes targeting (a) CYP2C9*2 SNP, (b) CYP2C9*3 SNP, and (c) VKORC1-1639G>A SNP. Error of $T_m$ measurement=±1° C.

First, the behavior of the nanoprobes in recognizing synthetic DNA targets was tested (SEQ ID Nos. 13-18 and FIG. 11). In the presence of ≥5 nM of targets that are either perfectly matched, a single-base mismatched, or their 1:1 mixture (representing heterozygous target), the nanoprobes became more stable and no color change was observed at room temperature even after 1 day of incubation with 50 mM of NaCl. As temperature rose, the $T_m$ values of the nanoprobe-target hybrids were obtained based on colorimetric signal. The $T_m$ generally increased with increasing target quantity. At any given target concentration, a single-base mismatch induced a nearly consistent decease in $T_m$.

Figure 12:
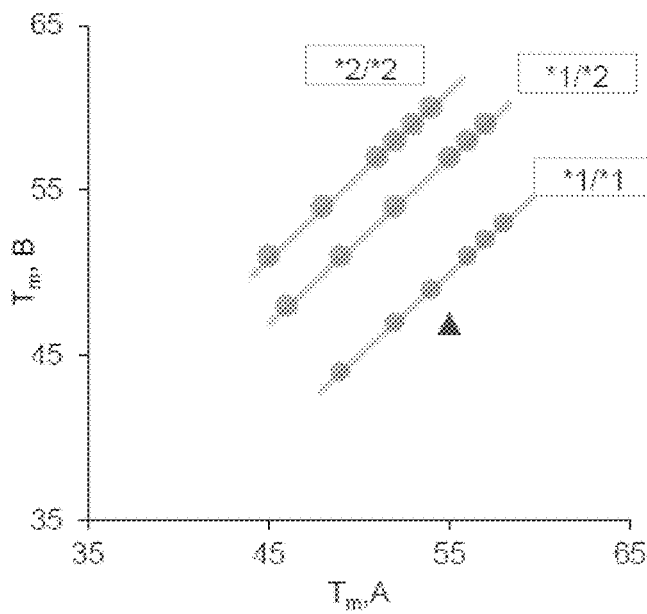
FIG. 12 shows scatter plots of $T_m^{WT}$ and $T_m^{MUT}$ of synthetic DNA targets (grey dots) and a human gDNA sample (red triangle) for the genotyping of (a) CYP2C9*2, (b) CYP2C9*3, and (c) VKORC1-1639. The three linear regions corresponding to specific genotypes are used to determine the genotypes of the human samples. Error of $T_m$ measurement=±1° C.
Figure 12:
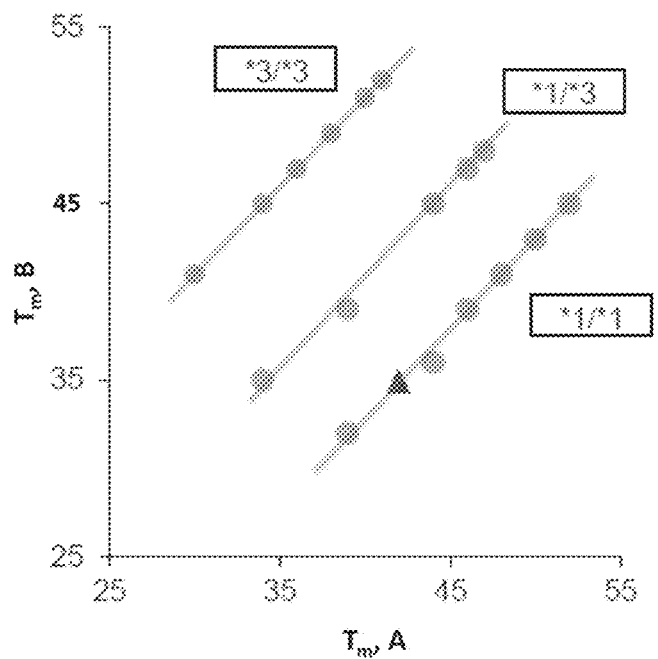
Figure 12:
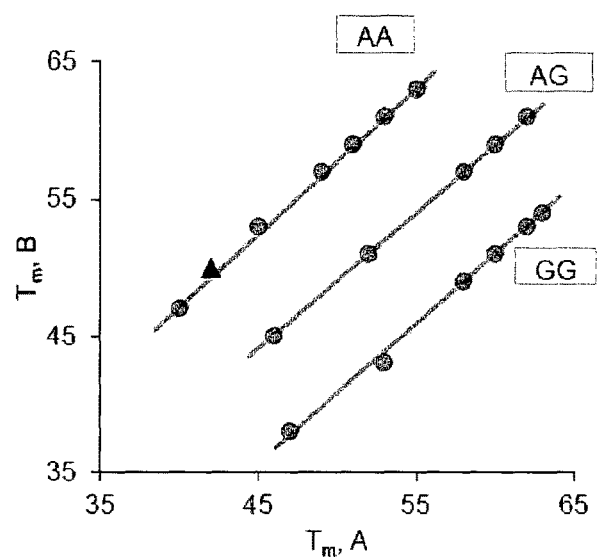

The $(T_m^{WT}-T_m^{MUT})$ scatter plots of each pair of nanoprobes are shown in FIG. 12. Over a relatively large concentration range of the synthetic targets (5 nM to 500 nM), 3 groups of data points corresponding to the 3 types of target sequences, respectively, were observed in their specific linear regions, distinctly separated from each other.

Figure 13:
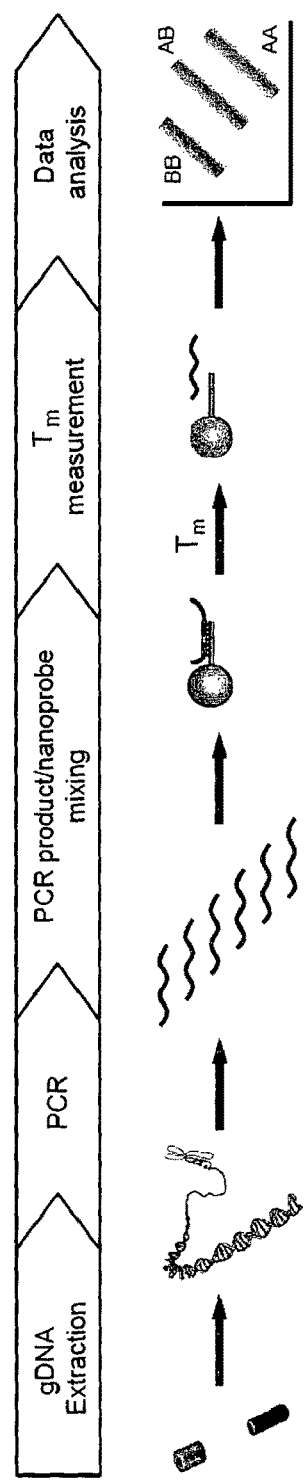
FIG. 13 shows a workflow of the nanoprobe-based genotyping for warfarin sensitivity test.

The new genotyping platform was examined in the analysis of human gDNA from the cheek swab of a healthy volunteer by implementing a simple workflow (FIG. 13). After extraction of gDNA from the sample with a commercial kit, aPCR was performed to generate ssDNA targets.

Figure 14:
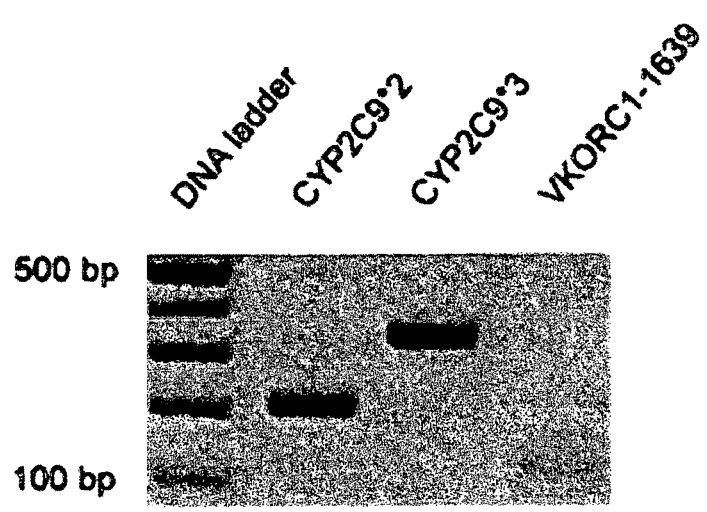
FIG. 14 shows a gel image of PCR products received during genotyping of warfarin.
Figure 15:
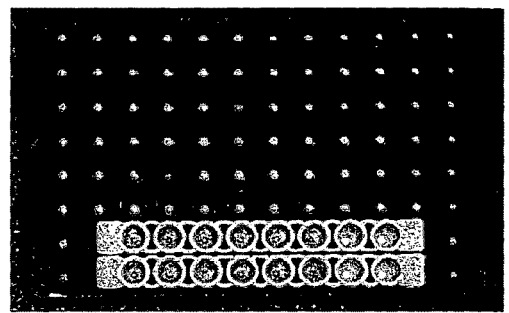
FIG. 15 (a) shows photographs of the setup for $T_m$ measurement on a thermal cycler. (b) Typical photographs recorded during $T_m$ measurement for warfarin genotyping. The according genotype assignment is shown in FIG. 17.
Figure 15:
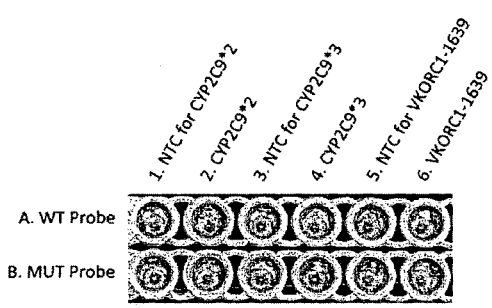
Figure 15:
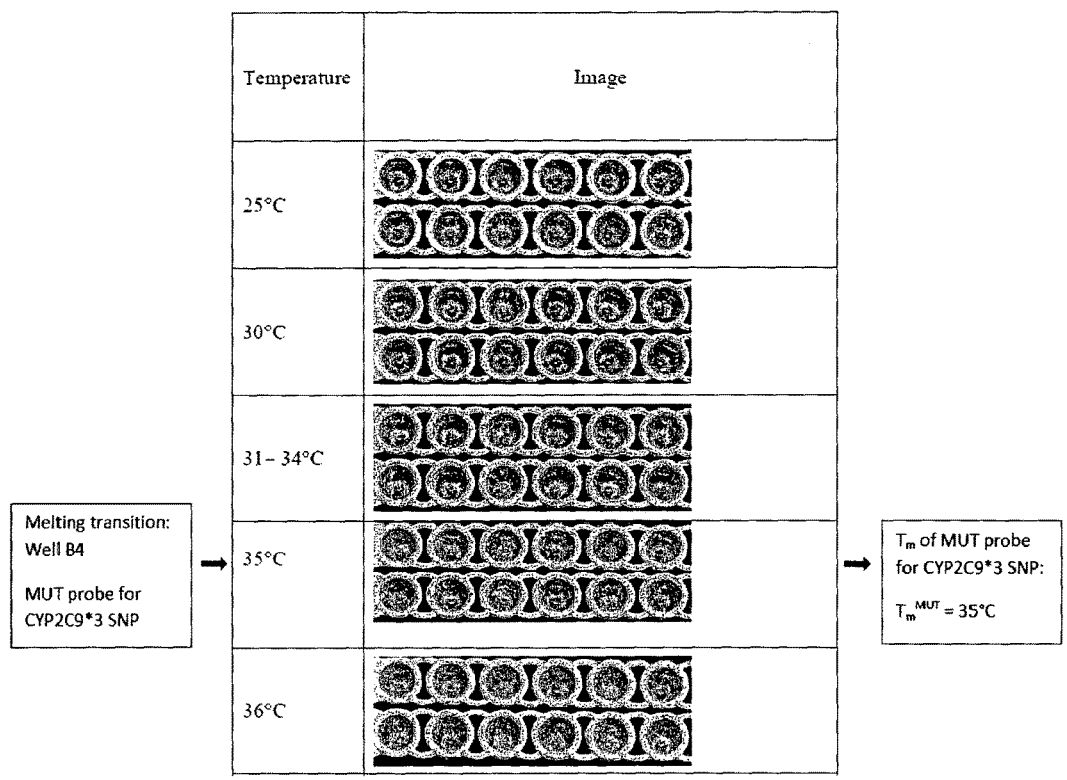
Figure 15:
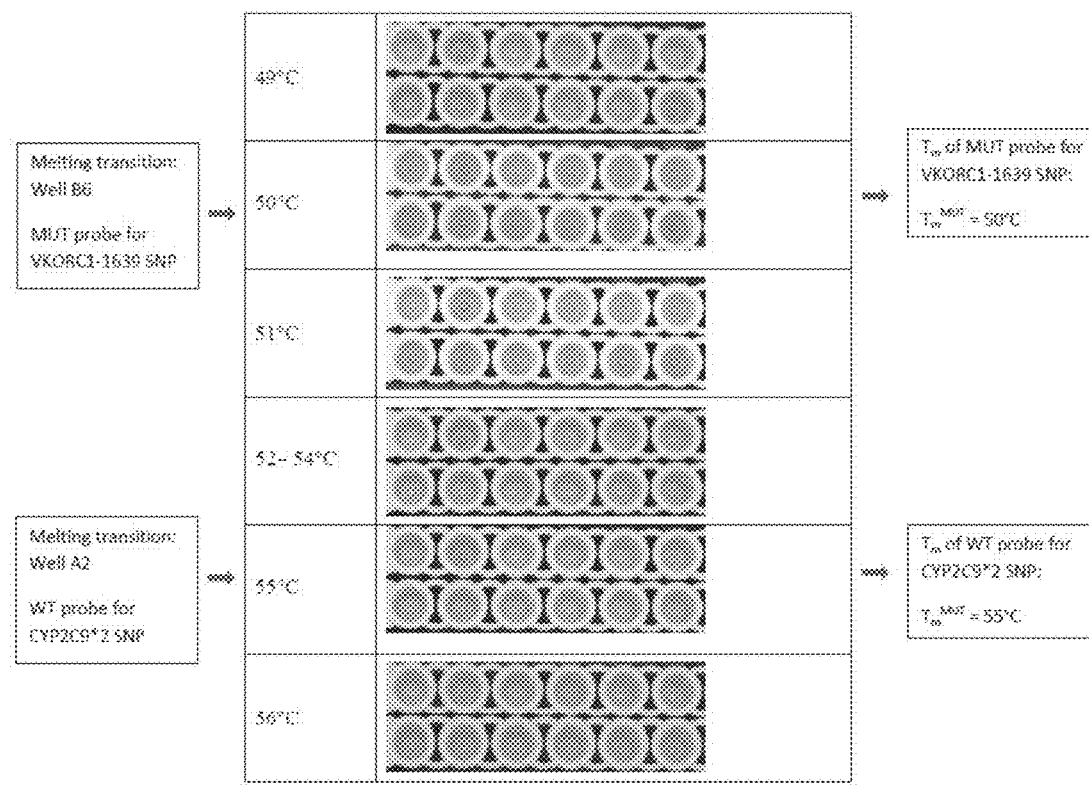
Figure 15:
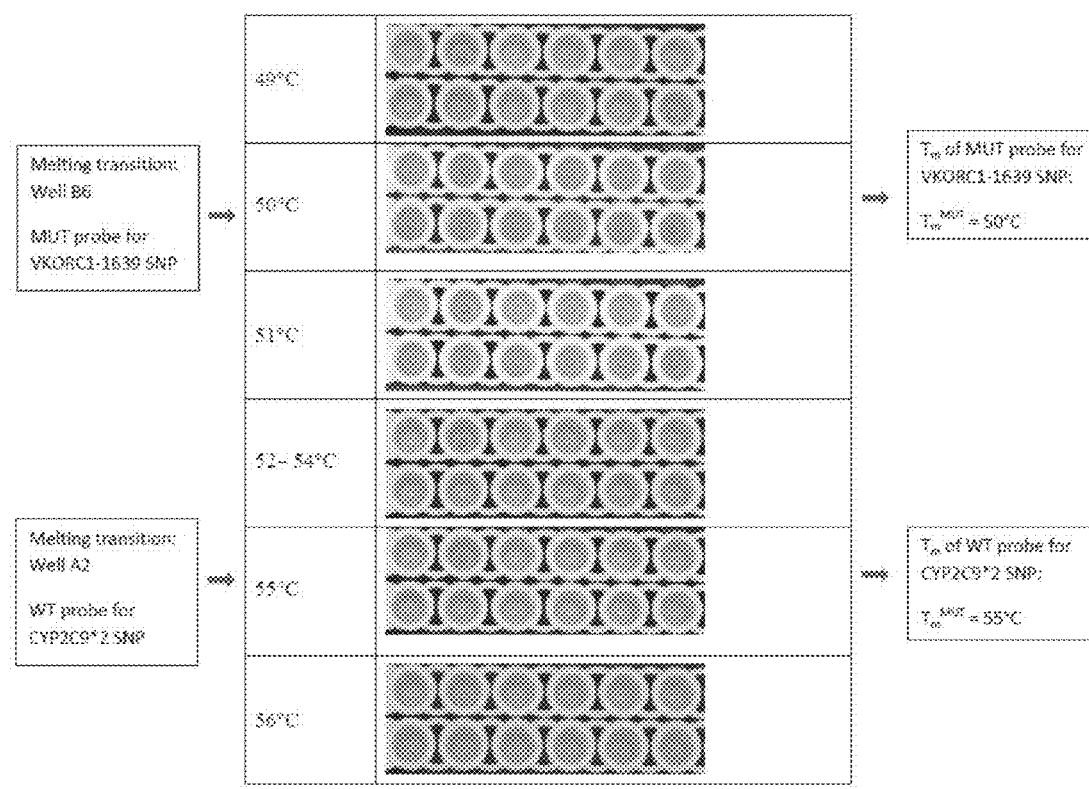

The assay involved 3 aPCR reactions to amplify the sequence fragments containing the SNPs. The primers were designed and optimized so that the amplifications could be conducted under an identical thermal cycling condition (SEQ ID Nos. 19-24 and FIGS. 14 and 16). Following aPCR, two aliquots of the products of each reaction were mixed with the specific WT and MUT probes, respectively. Next, $T_m$ values of the target/nanoprobe hybrids were measured based on the sharp melting transitions (FIGS. 15 and 17). By plotting the obtained $T_m$ data in the corresponding standard diagrams, the genotypes of the sample could be assigned (FIG. 12). The protocol did not include any purification and washing steps, and could be completed within 2 h.

To summarize the above and to compare the present invention with other genotyping platforms, it is noted that the nanoprobe-based technology exhibits some unique advantages. First, the simple solution-phase assay leads to highly reproducible results. The homogeneously dispersed nanoprobes hybridize with DNA targets in solution rapidly. Post-PCR clean-up and post-hybridization washing steps are not involved, greatly simplifying the detection and avoiding the need for stringent control over experimental conditions. Secondly, because of the extremely sharp melting transitions and the distinct color change, the nanoprobes are highly specific in recognizing DNA sequences, ensuring specificity and accuracy of the assay. Thirdly, the plasmonic nanoprobes permit inexpensive colorimetric detection, instead of fluorophore-based detection that requires sophisticated optics and algorithms. Since the only instrument required is a standard thermal cycler, the platform can be readily deployed in any laboratory with a PCR without further investment in capital equipment. In addition, the solution-phase assay can be easily integrated with a microfluidic system to miniaturize and automate the assay and achieve point-of-care testing.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. A method of detecting a mutation in a target nucleic acid molecule in sample, the method comprising:

(i) contacting a first conjugate comprising a first nanoparticle and a first oligonucleotide analog, wherein the first oligonucleotide analog is a phosphorodiamidate morpholino oligo or a derivative thereof that is covalently coupled to the first nanoparticle with an aliquot containing the target nucleic acid sequence, wherein the first oligonucleotide analog comprises a base sequence that is complementary to the wildtype sequence of the target nucleic acid, under conditions which allow the first conjugate and the target nucleic acid molecule to hybridize to each other, to form a first conjugate:target nucleic acid molecule complex;

(ii) contacting a second conjugate comprising a second nanoparticle and a second oligonucleotide analog, wherein the second oligonucleotide analog is a phosphorodiamidate morpholino oligo or a derivative thereof that is covalently coupled to the second nanoparticle with another aliquot containing the target nucleic acid sequence, wherein the second oligonucleotide analog comprises a base sequence that is complementary to a mutated sequence of the target nucleic acid and differs from the base sequence of the first oligonucleotide analog by at least one nucleobase and wherein the first and the second oligonucleotide analog have a sequence identity of at least 85%, under conditions which allow the second conjugate and the target nucleic acid molecule to hybridize to each other, to form a second conjugate:target nucleic acid molecule complex, and (iii) determining melting temperatures of the first complex and the second complex of (i) and (ii) and detecting whether said target nucleic acid molecule contains said mutation by comparing the melting temperatures of said first and second complexes, wherein the first oligonucleotide analog comprises the base sequence set forth in SEQ ID NO: 1 and the second oligonucleotide analog comprises the base sequence set forth in SEQ ID NO: 2.

2. The method according to claim 1 further comprising amplifying the target nucleic acid molecule by polymerase chain reaction previous to (i).

3. The method according to claim 1, wherein said sample is a heterogeneous sample.

4. The method according to claim 1, wherein the target nucleic acid molecule comprises the nucleotide sequence set forth in SEQ ID Nos. 3, 4, 13, 14, 15, 16, 17 or 18.

5. The method according to claim 1, wherein a monomeric unit of the phosphorodiamidate morpholino oligo or derivative thereof of either the first oligonucleotide analog or the second oligonucleotide analog is represented by formula (I)

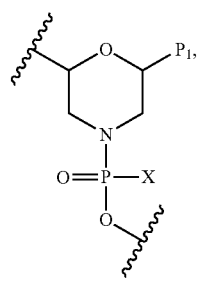

(I)

wherein
P1 is a purine or pyrimidine base capable of forming Watson-Crick base pairs with another purine or pyrimidine base; and
X is NH$_2$, NHR, or NR$_2$, wherein R is C1-C6 alkyl.

6. The method according to claim 5, wherein
(1) the other purine or pyrimidine base that forms Watson-Crick base pairs with the purine or pyrimidine base of P1 is a nucleobase;
(2) X is NR$_2$ and R is methyl;

(3) the P1 purine or pyrimidine base is a nucleobase selected from the group consisting of adenine, cytosine, guanine, thymine, and uracil; or (4) the P1 purine or pyrimidine base is a nucleobase selected from the group consisting of 5-methylcytosine, pseudouridine, dihydrouridine, inosine, 7-methylguanosine, xanthine, and hypoxanthine.

7. A kit comprising a first and second conjugate,
the first conjugate comprising a first nanoparticle and a first oligonucleotide analog, wherein the first oligonucleotide analog is a phosphorodiamidate morpholino oligo or a derivative thereof that is covalently coupled to the first nanoparticle, and
the second conjugate comprising a second nanoparticle and a second oligonucleotide analog, wherein the second oligonucleotide analog is a phosphorodiamidate morpholino oligo or a derivative thereof that is covalently coupled to the second nanoparticle,
wherein the first oligonucleotide analog differs from the second oligonucleotide analog by at least one nucleobase and wherein the first oligonucleotide analog has a sequence identity to the second oligonucleotide analog of at least 85%,
wherein
the first oligonucleotide analog comprises the base sequence set forth in SEQ ID NO: 1 and the second oligonucleotide analog comprises the base sequence set forth in SEQ ID NO: 2.

8. The kit according to claim 7, wherein the first and/or the second nanoparticle is a metal nanoparticle.

9. The kit according to claim 8, wherein the metal is a noble metal.

10. The kit according to 8, wherein the metal is selected from the group consisting of gold, silver, platinum, palladium, ruthenium, osmium, iridium, and mixtures thereof.

11. The kit according to claim 8, wherein the metal is gold.

12. The kit according to claim 7, wherein the diameters of the first and the second nanoparticles are in the range of about 1 nm to about 100 nm.

13. The kit according to claim 7, wherein a monomeric unit of the phosphorodiamidate morpholino oligo or derivative thereof of either the first oligonucleotide analog or the second oligonucleotide analog is represented by formula (I)

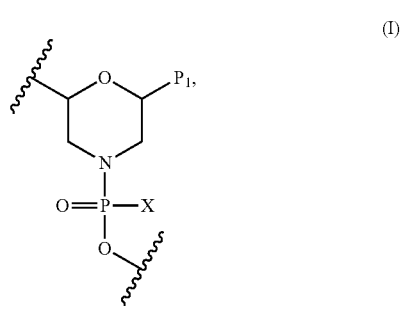

(I)

wherein
P1 is a purine or pyrimidine base capable of forming Watson-Crick base pairs with another purine or pyrimidine base; and
X is NH$_2$, NHR, or NR$_2$, wherein R is C1-C6 alkyl.

14. The kit according to claim 13, wherein the other purine or pyrimidine base that forms Watson-Crick base pairs with the purine or pyrimidine base of P1 is a nucleobase.

15. The kit according to claim 13, wherein X is NR$_2$ and R is methyl.

16. The kit according to claim 13, wherein the P1 purine or pyrimidine base is a nucleobase selected from the group consisting of adenine, cytosine, guanine, thymine, and uracil.

17. The kit according to claim 13, wherein the P1 purine or pyrimidine base is a nucleobase selected from the group consisting of 5-methylcytosine, pseudouridine, dihydrouridine, inosine, 7-methylguanosine, xanthine, and hypoxanthine.

18. The kit according to claim 7, wherein the first and second oligonucleotide analogs comprise about 15 to about 35 monomeric units.

19. The kit according to claim 7, wherein the at least one oligonucleotide analog is covalently coupled to the nanoparticle via a functional group.

20. The kit according to claim 7 further comprising PCR primers.

* * * * *